United States Patent [19]
Suyama et al.

[11] Patent Number: 5,963,042
[45] Date of Patent: Oct. 5, 1999

[54] METHOD FOR INSPECTING THE ELEMENTS OF PIPING SYSTEMS BY ELECTROMAGNETIC WAVES

[75] Inventors: Kiichi Suyama; Takashi Imaoka, both of Yokohama, Japan

[73] Assignee: Tokyo Gas Co., Ltd., Tokyo, Japan

[21] Appl. No.: 09/048,002

[22] Filed: Mar. 26, 1998

Related U.S. Application Data

[62] Division of application No. 08/687,450, Aug. 15, 1996.

[30] Foreign Application Priority Data

| Dec. 16, 1994 | [JP] | Japan | 6-313498 |
| Dec. 16, 1994 | [JP] | Japan | 6-313499 |
| Jul. 14, 1995 | [JP] | Japan | 7-179183 |
| Jul. 14, 1995 | [JP] | Japan | 7-179184 |
| Jul. 28, 1995 | [JP] | Japan | 7-192735 |
| Aug. 21, 1995 | [JP] | Japan | 7-211464 |
| Aug. 21, 1995 | [JP] | Japan | 7-211465 |
| Jul. 14, 1997 | [JP] | Japan | 7-179185 |

[51] Int. Cl.$^6$ .................................................. G01R 27/26
[52] U.S. Cl. ............................................. 324/637; 324/326
[58] Field of Search ...................... 324/326, 637, 324/642, 643, 647

[56] References Cited

U.S. PATENT DOCUMENTS 3,693,075  9/1972  Forster ..................................... 324/220
3,878,453  4/1975  Potter ......................................... 324/67

*Primary Examiner*—Maura Regan
*Attorney, Agent, or Firm*—Townsend & Banta

[57] ABSTRACT

Electromagnetic waves are driven in the pipe to be inspected in the piping system by a transmitting antenna of a transmitter, to be propagated in the pipe; while a receiving antenna of a receiver is moved outside the pipe along the pipe, to receive leaking electromagnetic waves for inspecting elements of the piping system, and the location concerned of each element of the piping system to be inspected is detected in reference to the location of the receiving antenna where the level of electromagnetic waves received by the receiver becomes a peak. The locations to be inspected are the damaged portions such as holes formed by corrosion, cracks, etc. in the pipes, and the locations of joints, etc. It is also possible to move the transmitting antenna outside along the pipe, while arranging the receiving antenna at proper place in the pipe. Furthermore, it is also possible to move both the transmitting antenna and the receiving antenna in synchronization to effect the above inspection. When either the transmitting antenna or the receiving antenna is moved, the frequency of electromagnetic waves can be a frequency propagated in the pipe or can also be lower than the cut-off frequency. On the other hand, the antenna can be made long and kept in the pipe, to use a frequency lower than the cut-off frequency without moving the antenna

20 Claims, 18 Drawing Sheets

METHOD FOR INSPECTING THE ELEMENTS OF PIPING SYSTEMS BY ELECTROMAGNETIC WAVES

CROSS REFERENCE TO A RELATED APPLICATIONS

This is a divisional application of co-pending application Ser. No. 08/687,450 filed Aug. 15, 1996.

TECHNICAL FIELD

The present invention relates to a method for inspecting the piping systems used to supply city gas, etc. mainly buried under roads, etc. or installed in the walls, floors, etc. of buildings, hence not exposed outside, by use of electromagnetic waves, to detect, for example, damaged portions such as holes formed by corrosion in the pipes as one of an element of piping system, and the locations of joints as another elements of piping system, etc.

BACKGROUND OF THE INVENTION

The gas leak from a hole formed by corrosion, etc. in a gas pipe not exposed outside like a buried pipe in the piping system of a city gas supply network is conventionally inspected by using various methods such as the sense of smell or a gas detector, or boring work in combination with the foregoing means, etc. If gas leak is detected in reference to the smell or in periodical inspection, the ground is dug or the wall is removed, to exchange or repair the gas pipe.

However, in the conventional methods, since any component of the gas itself or an odorous component added beforehand to the gas which leaks and diffuses from a damaged portion of the gas pipe is detected by using a gas detector or the human sense of smell, to identify the fact of leak and the location of leak, the occurrence of gas leak and its location cannot always accurately detected.

For example, if a cavity is formed in parallel to a gas pipe installed underground or inside a wall, etc., it can happen that the gas leaking from a damaged portion of the gas pipe migrates through the cavity and diffuses into air or indoor, etc. at a position apart from the damaged portion, and in this configuration, it can happen that the position apart from the actually damaged portion is detected as the damaged portion by error. If excavation or wall removal, etc. is effected as mentioned above based on the wrong information, the work is wasteful, and second and even third work may be required disadvantageously. Furthermore, if the gas leaking from a damaged portion of a gas pipe is retained near the damaged portion without diffusing in air or indoor, etc., the leak itself may not be able to detected.

As described above, the method of inspecting the occurrence of leak and the damaged portion by detecting any component of the gas itself or the odorous component added beforehand to the gas leaking and diffusing from the damaged portion cannot always accurately detect the occurrence of leak and its location.

On the other hand, one of conventional general inspection methods for detecting the damage of metallic structures is ultrasonic flaw detection, but it is difficult to apply this method for inspection of piping systems not exposed, for such reasons that the probe must be kept in tough with the object to be inspected, and that flaw detection for a long distance cannot be made.

An object of the present invention is to overcome the above mentioned disadvantages of the conventional inspection methods, and to provide an inspection method which can relatively accurately detect damaged portions of pipes such as holes formed by corrosion, when applied to the inspection of elements of piping systems, particularly metallic piping systems not exposed.

Another object of the present invention is to provide an inspection which can measure the distances of piping systems to damaged portions and can detect the locations and states of some joints as other elements of piping systems, in addition to the detection of damaged portions of pipes.

DISCLOSURE OF THE INVENTION

The inspection method of the present invention comprises the steps of driving electromagnetic waves at a proper place of the pipe to be inspected of a piping system, by a transmitting antenna of a transmitter, for propagating the electromagnetic waves in the pipe; moving a receiving antenna of a receiver along the pipe outside, to receive leaking electromagnetic waves for inspecting the elements of the piping system; and detecting an intended location of an element of the piping system inspected, in reference to the location of the receiving antenna at which the level of received electromagnetic waves becomes a peak.

In this configuration, the electromagnetic waves propagated in a pipe do not usually leak outside, but if there is any damaged portion such as a hole formed by corrosion or crack, etc. in the pipe, the electromagnetic waves leak from the portion, and are detected by the receiving antenna, to allow the damaged portion to be identified. The leak of electromagnetic waves may occur not only such damaged portions but also at joints, and in this configuration, joints can also be detected. The level of received leaking electromagnetic waves in the receiver becomes highest when the receiving antenna is at a location nearest to any object to be detected such as a damaged portion or joint if the receiving antenna is non-directional or moves in parallel in its direction. So, at the location of the receiving antenna at which the level of the received waves becomes a peak, the damaged portion or joint location of the piping system buried under a road, etc. or installed in the wall or under the floor, etc. of a building, hence not exposed outside can be accurately detected.

In the present invention configured as above, the transmitting antenna is provided as a coaxially formed antenna with a probe protruded at the center and external threads formed around its outside member is installed in the antenna installation hole which is a hole drilled with internal threads formed in the wall of the pipe to be inspected of a piping system. In another version, an end of the pipe to be inspected of a piping system is cut off, and a coaxially formed antenna with a probe protruded coaxially is mounted on the cover to close the end, said cover being installed at the end. In a further other version, a probe is protruded inside the cover to close the central branch opening of a Tee installed on the extension of the pipe to be inspected of a piping system, and the probe and an electromagnetic wave generator are connected by a coaxial cable, with the probe located in the Tee when the cover is installed. In a still further other version, a loop is protruded inside the cover to close the central branch opening of a Tee installed on the extension of the pipe to be inspected of a piping system, and the loop and an electromagnetic wave generator are connected by a coaxial cable, with the loop located in the Tee when the cover is installed.

By any of the above means, the transmitting antenna can be easily installed in the pipe to be inspected of a piping system, and especially when a Tee is installed on the extension of a pipe of the piping system, pipe drilling work and cutting work are not required. Therefore, when the piping system to be inspected is, for example, a city gas supply system, the installation of the transmitting antenna and subsequent inspection as described above can be effected without stopping the supply of gas. Also when the transmitting antenna is installed in a hole drilled in the wall of a pipe, the antenna can be installed without stopping the supply of gas. These means for installing the transmitting antenna can also be applied to the methods described later for installing the receiving antenna at a proper place of a pipe of a piping system.

In the present invention, the receiving antenna is moved outside the piping system as described before, and for inspection, the transmitting antenna is moved inside the pipe of the piping system in connection with the movement of the receiving antenna, for generating electromagnetic waves.

In this configuration, the level of the electromagnetic waves received by the receiver near the location to be detected changes greatly to make the peak more outstanding, for enhancing the detection accuracy of the location to be detected in reference to the peak.

In the above method of the present invention, the frequency of electromagnetic waves is continuously or stepwise changed over time.

Since this does not allow any fixed electromagnetic field distribution to be formed in the pipe, the leak of electromagnetic waves from the location to be detected can be reliably identified, to allow reliable detection of the location to be detected.

In the present invention, the reception of leaking electromagnetic waves by the receiver is effected when the transmission of electromagnetic waves by the transmitter is in ON state and also when the transmission of electromagnetic waves by the transmitter is temporarily in OFF state, to identify the leaking electromagnetic waves by comparing the signals received in OFF state with the signals received in ON state. The ON-OFF control means can be provided in the transmitter, and a remote control switch for the ON-OFF control means can be provided in the receiver, to allow the ON-OFF control means to be operated from the receiver. Otherwise, the ON-OFF control means can be provided in the transmitter for ON-OFF control from the transmitter, and the signals synchronous with the ON-OFF actions can be transmitted to the receiver, to allow the ON and OFF states to be detected by the receiver.

In this configuration, the receiving antenna outside the piping system can reliably identify whether any electromagnetic waves received are leaking from said location concerned or external noise only.

In the present invention configured as above, the electromagnetic waves propagated by the transmitter in the piping system to be inspected are modulated. The modulation of electromagnetic waves can be used as a method for changing the frequency of electromagnetic waves over time described before and also as a method for turning on and off the transmission of electromagnetic waves by the transmitter.

In this configuration, if the electromagnetic waves as carrier waves are modulated by human recognizable information signals such as audio signals or visual signals, whether the electromagnetic waves received by the receiver are the electromagnetic waves transmitted by the transmitter or noise can be easily discriminated.

In another version of the present invention, the transmitting antenna of the transmitter can be moved along a pipe outside the piping system to be inspected, to transmit electromagnetic waves from the outside of the piping system. In this case, the receiving antenna of the receiver is fixed at a proper place of the pipe, or is moved in relation with the movement of the transmitting antenna, to receive the electromagnetic waves introduced into the piping system from outside, for inspecting the elements of the piping system. This method can be used as a method for changing the frequency of electromagnetic waves over time, as a method for turning on and off the transmission of electromagnetic waves by the transmitter and also as a method for modulating the electromagnetic waves respectively described before.

In this configuration, the electromagnetic waves transmitted from outside are introduced into the piping system from the location to be detected, propagated in the pipe and received by the receiver through the receiving antenna, to allow the location concerned to be identified. Since the level of the electromagnetic waves introduced from the location to be detected and received by the receiver becomes highest when the transmitting antenna is at a location nearest to the location to be detected, the location to be detected of the piping system can be accurately detected in reference to the location of the transmitting antenna at which the level of received electromagnetic waves becomes a peak.

In the present invention, the electromagnetic waves transmitted into a pipe by the transmitter are modulated, and the electromagnetic waves received by the receiver and the electromagnetic waves transmitted by the transmitter are compared in terms of modulated signals, to obtain the time difference. From the time difference, the propagation time corresponding to the distance remaining after subtracting the propagation distance from the transmission point to the leak point is subtracted, to measure the propagation time of electromagnetic waves from the transmission point to the leak point, for obtaining the distance of the piping system from the transmission point to the leak point. In this case, the time difference can be measured in reference to the phase difference between the electromagnetic waves detected by the transmitter and those transmitted by the transmitter in terms of modulated signals, and pulse compression can be applied to the electromagnetic waves when they are transmitted to the transmitter and to the electromagnetic waves when they are received by the receiver.

As described above, the location to be detected such as a damaged portion or a joint of a pipe in a piping system can be detected, and in addition, the distance from a reference location properly set in the piping system to a leak point can be measured.

In the methods described above, the electromagnetic waves transmitted by the transmitter are propagated through a pipe of the piping system concerned at a frequency higher than the cut-off frequency for the pipe used as a wave-guiding channel of electromagnetic waves, but in the following two versions of the present invention, the frequency is kept lower than the cut-off frequency.

In one of the versions of the present invention, while the transmitting antenna of the transmitter is moved in the pipe to be inspected of a piping system, electromagnetic waves are transmitted at a frequency lower than the cut-off frequency for the pipe used as a wave-guiding channel of the electromagnetic waves, and the receiving antenna of the receiver is moved in relation with the movement of the transmitting antenna, to receive leaking electromagnetic waves for inspection of elements of the piping system. In this case, the location to be detected of an element of the piping system to be inspected is detected in reference to the location of the transmitting antenna at which the level of the electromagnetic waves received by the receiver becomes a peak.

In this configuration, since the electromagnetic waves from the transmitting antenna are attenuated greatly without being propagated in the pipe, the quantity of the electromagnetic waves leaking from the location to be detected such as a damaged portion or joint of the pipe becomes largest when the transmitting antenna is nearest to the location to be detected. Therefore, the level of electromagnetic waves received by the receiver is very large when the transmitting antenna is near the location to be detected, to make the peak more outstanding, thereby enhancing the detection accuracy of the location concerned by the peak.

In the other version of the present invention, while the transmitting antenna of the transmitter is moved along a pipe outside the piping system to be inspected, electromagnetic waves are transmitted from outside the piping system at a frequency lower than the cut-off frequency for the pipe used as a wave-guiding channel of the electromagnetic waves, and the receiving antenna of the receiver is moved in the pipe in relation with the movement of the transmitting antenna, to receive the electromagnetic waves introduced into the pipe from outside, for inspection of elements of the piping system. In this case, the location to be detected of an element of the piping system to be inspected is detected in reference to the location of the receiving antenna at which the level of electromagnetic waves received by the receiver becomes a peak.

In this configuration, since the electromagnetic waves introduced from the transmitting antenna through the location to be detected are not propagated in the pipe, the quantity of leak is largest when the receiving antenna is nearest to the location to be detected. Therefore, also in this case, the level of electromagnetic waves received by the receiving antenna becomes very large when the receiving antenna is near the location to be detected, to make the peak more outstanding, for enhancing the detection accuracy of the location to be detected by the peak.

Also in these two versions of the present invention as in the previous versions of the present invention, if the electromagnetic waves as carrier waves are modulated by proper information signals, whether the electromagnetic waves received are the electromagnetic waves transmitted by the transmitter or noise can be easily discriminated.

In a still further other version of the present invention, a long transmitting antenna composed of many directional radiating parts arranged in the directions perpendicular to the axis and ranged in the axial direction is inserted in an inspection range of the pipe to be inspected of a piping system, to radiate electromagnetic waves in the pipe by the transmitter, and a receiving antenna of a receiver is moved along the pipe in the inspection range outside the piping system, to receive leaking electromagnetic waves, for inspection of elements of the piping system. In this case, the location to be detected of an element of the inspection system to be inspected is detected in reference to the location of the receiving antenna at which the level of electromagnetic waves received by the receiver becomes a peak.

In a still further other version of the present invention, contrary to the above version, a long receiving antenna composed of many directional radiating parts arranged in the directions perpendicular to the axis and ranged in the axial direction is inserted in an inspection range of the pipe to be inspected of a piping system, and is connected with a receiver, and a transmitting antenna of a transmitter is moved in the inspection range outside the piping system to be inspected, to transmit electromagnetic waves from outside the piping system, so that the receiver may receive the electromagnetic waves introduced from outside into the pipe. In this case, the location to be detected of an element of the piping system to be inspected is detected in reference to the location of the transmitting antenna at which the level of electromagnetic waves received by the receiver becomes a peak.

By any of the above means, as in these two inventions described before, the frequency of the electromagnetic waves transmitted by the transmitting antenna can be lower than the cut-off frequency determined by the diameter of the pipe of the piping system, to allow to decrese the influence of the attenuation of the electromagnetic waves by the soil or concrete, etc. for inspecting the buried piping system. Moreover, the necessity of the synchronous movements of the transmittig antenna and the receiving antenna is eliminated in comparison with these aforesaid two inventions.

In the above two versions of the present invention, the long antenna can be a long helical antenna, leakage coaxial cable or twisted pair leakage cable with its directions kept perpendicular to the axis.

In the present invention described above, an element to be inspected of a piping system is, first of all, a pipe, and in this case, the location to be detected is a damaged portion such as a hole formed by corrosion in the pipe. Another element to be inspected is a joint not exposed, and in this case the location to be inspected is the location of the joint itself Furthermore, in the present invention, when a joint is the element to be inspected, not only its location but also the condition of the joint can be estimated in reference to the level of electromagnetic waves received by the receiver.

In the present invention as described above, the transmitter can be provided with a device for adjusting the intensity of the electromagnetic waves transmitted, and if the adjusting device is used to adjust in response to the level of electromagnetic waves received by the receiver for example, the peak can be easily detected at a proper level of electromagnetic waves received.

THE MOST PREFERRED EMBODIMENTS OF THE INVENTION

The present invention is described below in more detail in reference to the attached drawings.

Figure 1:
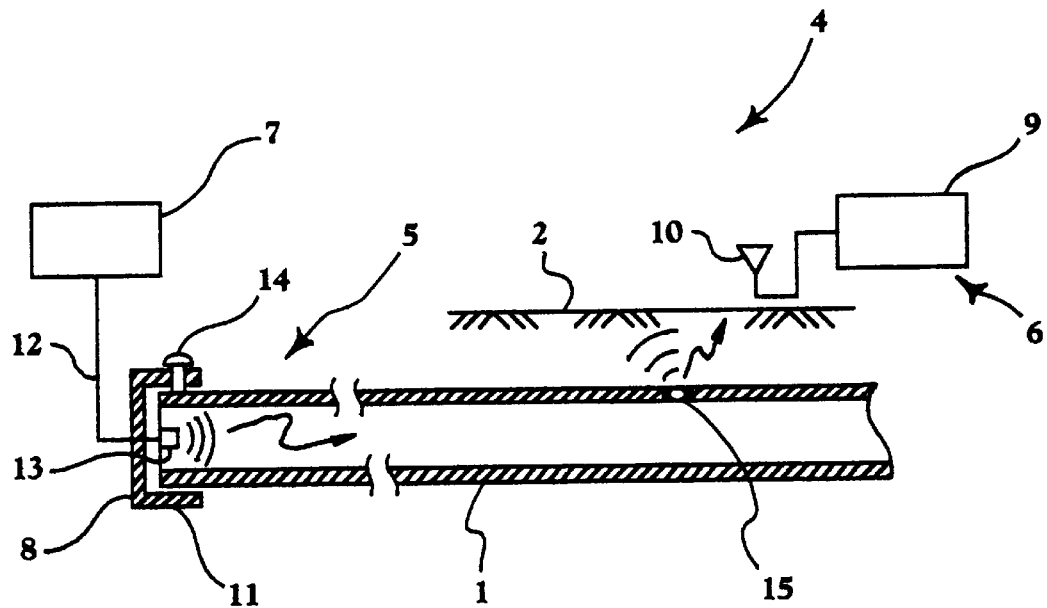
FIG. 1 is an illustration conceptually showing an embodiment of the present invention.
Figure 2:
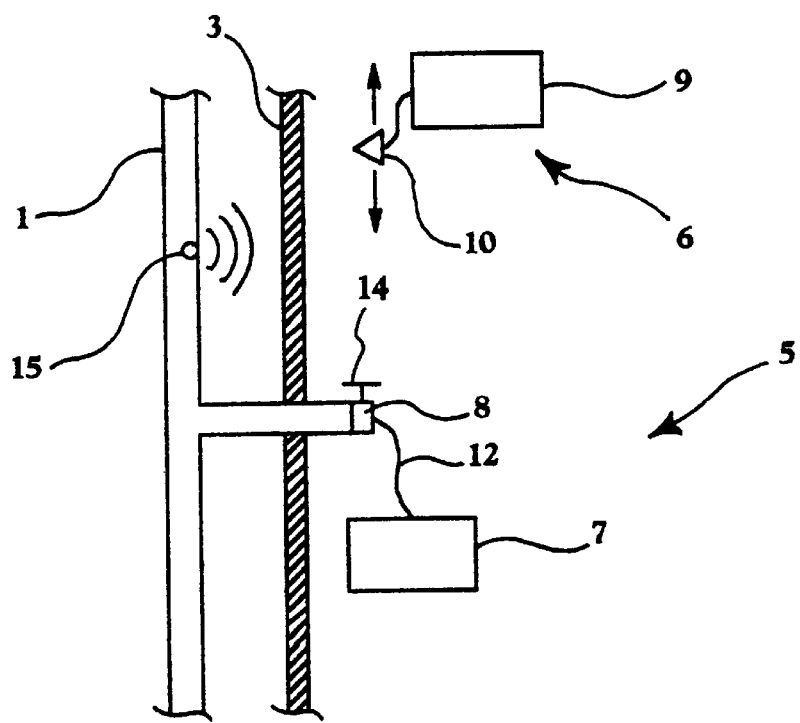
FIG. 2 is an illustration conceptually showing another embodiment of the present invention.

FIG. 1 conceptually shows an embodiment of the present invention. Symbol 1 denotes a pipe as an element to be inspected of a piping system, and the pipe 1 in this drawing is buried underground 2. FIG. 2 conceptually shows another embodiment, and the pipe 1 in this drawing is installed inside a wall 3 of a building.

The piping systems which can be inspected by applying the present invention include city gas supply systems as described above, and also piping systems of chemical plants, piping systems for heat exchanges of electric power plants, water supply pipes, etc., and the present invention can be effectively applied to piping systems buried underground such as under roads or installed in the walls or under the floors of buildings, hence not exposed outside.

Symbol 4 generally denotes an inspection apparatus to which the present invention is applied. The inspection apparatus 4 is generally composed of a transmitter S and a receiver 6, and the transmitter 5 is composed of a transmitter proper 7 and a transmitting antenna 8 to be installed at an end of the pipe 1, i.e., a means for driving electromagnetic waves into the pipe 1. The receiver 6 is composed of a receiver proper 9 and a receiving antenna 10, and the receiving antenna 10 can move.

To describe the configuration of the illustrated transmitting antenna 8, the transmitting antenna 8 has an antenna proper 13 protruded at the center inside a metallic cover 11 to close the end of the pipe 1 and connected with the transmitter proper 7 through a coaxial cable 12, and when the transmitting antenna 8 is fixed at the end of the pipe 1 by a screw 14 provided at a proper place of the cylindrical portion of the cover 11, the antenna proper 13 is arranged almost at the center of the pipe 1. The antenna proper 13 is a probe or loop, etc. which excites electromagnetic waves, to propagate them in a predetermined mode. The other most preferred embodiments of the transmitting antenna 8 (or receiving antenna) will be described later in detail.

The receiving antenna 10 can be moved manually or on a carriage, etc. Furthermore, the receiving antenna 10 can be moved separately from the receiver proper 9 or can be mounted integrally with the receiver proper 9, to be moved with the receiver proper 9.

In the above configuration, when the pipe 1 buried underground as shown in FIG. 1 or the pipe 1 installed in the wall 3 as shown in FIG. 2 is inspected, the pipe 1 is cut off at a portion exposed in space, etc. on an extension (or a branch) of the pipe 1, and the transmitting antenna 8 is installed at the end. Then, electromagnetic waves are supplied from the generation means of the transmitter proper 7 through the coaxial cable 12 to the transmitting antenna 8, and are driven in the pipe 1 in a mode corresponding to the arrangement of the transmitting antenna proper 13, etc., to be propagated in the pipe 1. That is, if electromagnetic waves of a predetermined frequency are supplied from the transmitter proper 7 to the transmitting antenna 8, the pipe 1 acts as a wave guiding channel similar to a circular waveguide for the electromagnetic waves, and the electromagnetic waves can be propagated in a predetermined mode at a frequency higher than the cut-off frequency.

For example, when the electromagnetic waves are driven in $TE_{11}$ mode which is the propagation mode of the lowest order by the transmitting antenna proper 13, the frequency of the electromagnetic waves supplied to the transmitting antenna proper 13 is made higher than the cut-off frequency represented by the following formula:

Cut-off frequency=Light velocity/Cut-off wavelength≈Light velocity/{ 1.706×Inner diameter of pipe 1 }

For example, the cut-off frequency of a pipe of 100 mm inner diameter is about 1.8 GHz, the cut-off frequency of a pipe of 80 mm in inner diameter, about 2.2 GHz, and the cut-off frequency of a pipe of 50 mm in inner diameter, about 3.5 GHz. The cut-off frequencies are peculiar to $TE_{11}$ mode, and in other propagation modes such as $TE_{01}$, $TM_{01}$, . . . modes, respectively different peculiar cut-off frequencies exist.

While electromagnetic waves are propagated in the pipe 1 by the transmitter 5, the receiving antenna 10 of the receiver 6 is moved along the pipe 1 outside, for receiving the electromagnetic waves. To move the receiving antenna 10 along the pipe 1 buried underground 2 or installed in the wall 3, etc., hence not exposed, a piping diagram or design drawing, or a pipe locator, etc. can be used.

The electromagnetic waves propagated in the pipe 1 as described above do not leak outside in the normal portions of the pipe 1, but if there is any damaged portion 15 such as a hole formed by corrosion or a crack, etc., they leak from the portion to outside.

Therefore, the damaged portion 15 can be detected by receiving the leaking electromagnetic waves by the receiver 6 through the receiving antenna 10. The level of the electromagnetic waves received by the receiver 6 is highest when the receiving antenna 10 is nearest to the damaged portion 15 if the receiving antenna 10 is non-directional or if the receiving antenna 10 is sharply directional and moved in parallel with its direction turned toward the pipe 1. Therefore, the location of the receiving antenna 10 at which the level of electromagnetic waves received by the receiver 4 becomes a peak can be detected as the location of the damaged portion 15. That is, when the pipe 1 is buried, the location below the receiving antenna 10 at which the level of electromagnetic waves received becomes a peak can be identified as the location of the damaged portion 15, and also when the pipe 1 is installed in the wall 3, etc., the location can be identified similarly.

Figure 3:
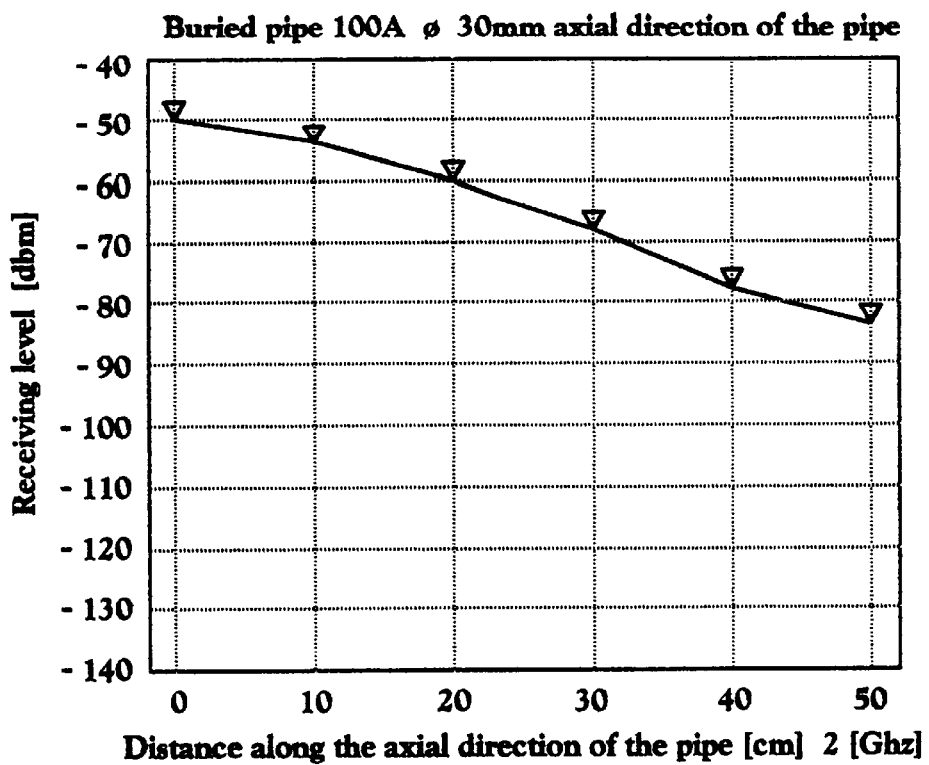
FIGS. 3 and 4 are graphs showing the results of tests to detect a drilled hole of a test pipe by applying the present invention.
Figure 4:
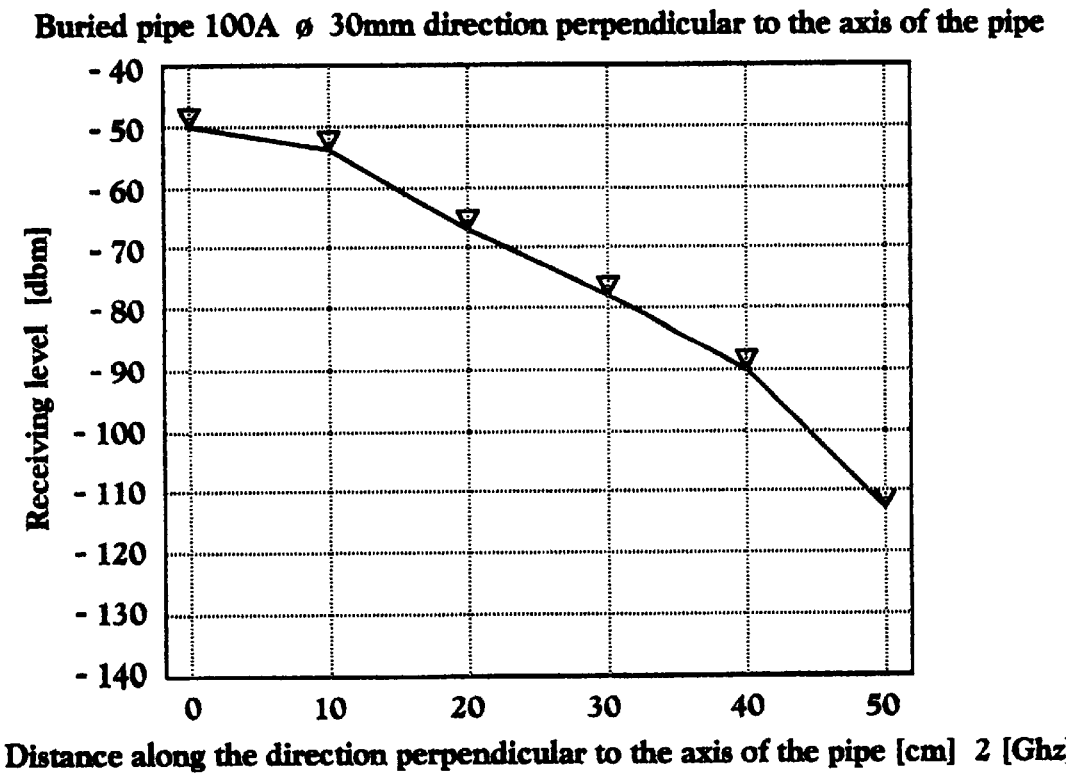

A test pipe of 100 mm in inner diameter with a 30 mm dia. hole drilled as an artificial defect on the top side was buried under a 10 cm thick concrete layer (with reinforcing bars at the bottom), 10 cm thick crushed stone layer and 10 cm thick soil layer in this order from the ground surface, and from the pipe end, electromagnetic waves of 2 GHz in frequency and 25 dbm were driven and propagated, while the receiving antenna was moved on the ground surface in the axial direction of the pipe and in the direction perpendicular to the axis, to receive the electromagnetic waves leaking from the hole of the pipe. The levels measured are shown in FIGS. 3 and 4. FIG. 3 shows a case of moving the antenna in the axial direction of the pipe, and FIG. 4, a case of moving the antenna in the direction perpendicular to the axis. In both the cases, the distance 0 on the abscissa indicates that the receiving antenna arrived at the location right above the hole.

From the results, it can be seen that since the level of electromagnetic waves received becomes highest, i.e., a peak when the receiving antenna is nearest to the hole, the location of the hole can be detected in response to the peak.

The level of electromagnetic waves received can be confimed in reference to the reading on a level meter or the volume or frequency can be changed in response to the level of electromagnetic waves received, to allow confirmation in reference to sound.

Furthermore, if the electromagnetic waves driven and propagated in the pipe are modulated by human recognizable information signals such as audio signals or visual signals by the transmitter proper 7, to contain the information signals, and demodulated by the receiver proper 9 for output, then the output allows easy confirmation that the received electromagnetic waves are predetermined electromagnetic waves distinguished from noise. This can be achieved by letting the transmitter proper 7 have such components as a modulator and amplifier, and the receiver proper 9 have such components as a detector, demodulator, amplifier, monitor, speaker, etc. These are not illustrated in the drawings.

On the other hand, in the above inspection action, it is preferable that the electromagnetic waves leaking from the damaged portion 15 of the pipe 1 by the receiver 6 always at a proper receiving level not affected by the environment where the pipe 1 is installed. If the pipe 1 is buried underground, it may be buried at a different depth or in different soil, and if the pipe 1 is installed in the wall, it may be differently apart from the receiving antenna while the material existing between them may be different. Therefore, if electromagnetic waves are transmitted always at the same level and received at the same sensitivity, the level of electromagnetic waves received cannot be always appropriate.

So, the transmitter 5 is provided with a device (not illustrated) for adjusting the intensity of the electromagnetic waves to be transmitted from it. The adjusting device allows level adjustment to ensure reliable inspection without making the level transmitted too high to suit the capacity of the receiver or without affecting the surrounding as noise. In this configuration, in the beginning of inspection, the electromagnetic waves transmitted from the transmitter 5 are set at a high level, and the receiving sensitivity of the receiver 6 is also set at a high level. If the electromagnetic waves are always received in this state, the level transmitted is lowered, or the receiving sensitivity is lowered to conduct the inspection as described above.

As a result of the inspection, if the electromagnetic waves are received in a wide moving range of the receiving antenna 8, not allowing the peak of the level of electromagnetic waves received to be identified, the level transmitted is gradually lowered, to narrow the receiving range of the electromagnetic waves, for detection of a peak. In this way, the leak portion of electromagnetic waves, i.e., the location of the damaged portion 15 can be accurately detected. The adjustment of the level transmitted can also be effected in response to the level of electromagnetic waves received, by connecting the transmitter 5 and the receiver 6 by any wireless or wired communication means.

As described above, the frequency of the electromagnetic waves supplied to the transmitting antenna 8 are only required to be properly higher than the cut-off frequency corresponding to the propagation mode, but since a higher frequency is attenuated more in soil generally, the frequency is preferably set at a level as low as possible in this regard. Therefore, when the element to be inspected of a piping system is a buried pipe, the frequency of the electromagnetic waves driven and propagated in the pipe is preferably closer to said cut-off frequency. However, since there may be a pipe smaller in inner diameter than the other pipes of the piping system, the frequency of electromagnetic waves is preferably properly higher than the cut-off frequency to allow propagation also in the pipe.

Other embodiments of the transmitting antenna for driving and propagating electromagnetic waves to the pipe 1 to be inspection are described below.

Figure 5:
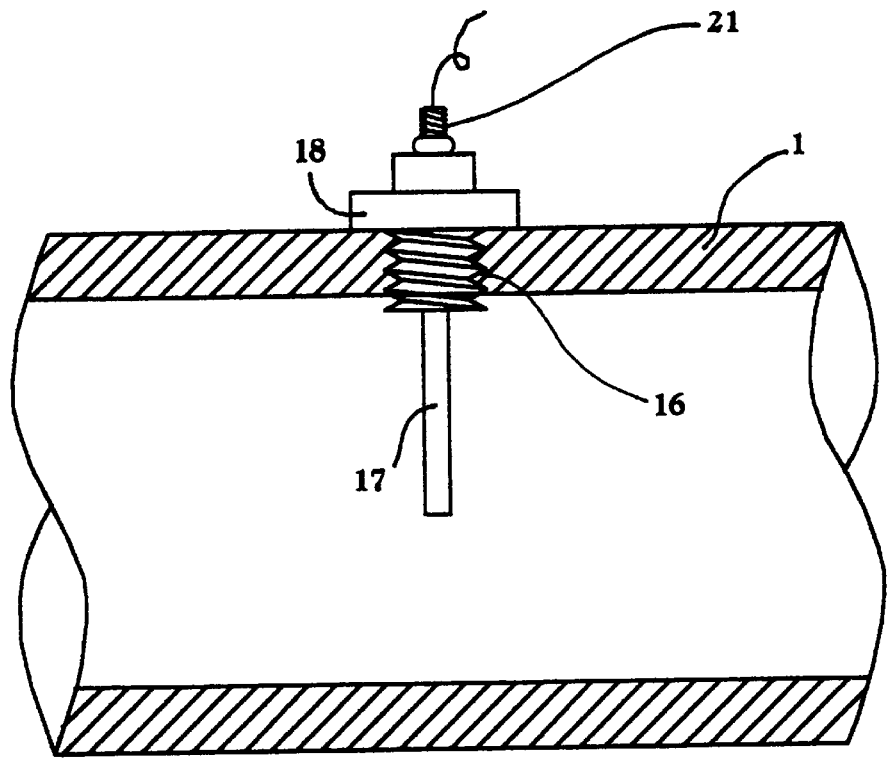
FIG. 5 is a sectional view showing an antenna attached to a pipe.
Figure 6:
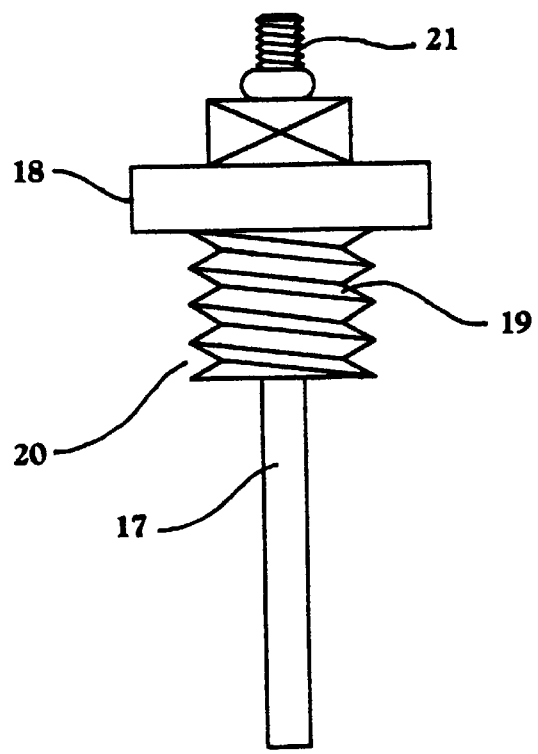
FIG. 6 shows an essential portion of FIG. 5.

In the transmitting antenna shown in FIGS. 5 and 6, a hole is drilled in the wall of the pipe 1 to be inspected of a piping system, and internal threads are formed in the hole, for use as an antenna installation hole 16. A coaxially formed antenna 20 with a probe 17 protruded at the center and external threads 19 formed around an outside member 18 is fitted in the antenna installation hole 16 by keeping the external and internal threads engaged with each other, to locate the probe 17 in the pipe 1. At the rear of the outside member 18, a coaxial connector 21 is provided.

In this configuration, since the pipe 1 is not required to be cut off unlike the case shown in FIG. 1, the transmitting antenna can be installed easily. Furthermore, if the pipe 1 is a city gas supply pipe, the transmitting antenna can be installed without stopping gas supply.

FIGS. 7 through 12 show other embodiments of the transmitting antenna different from the above.

Figure 7:
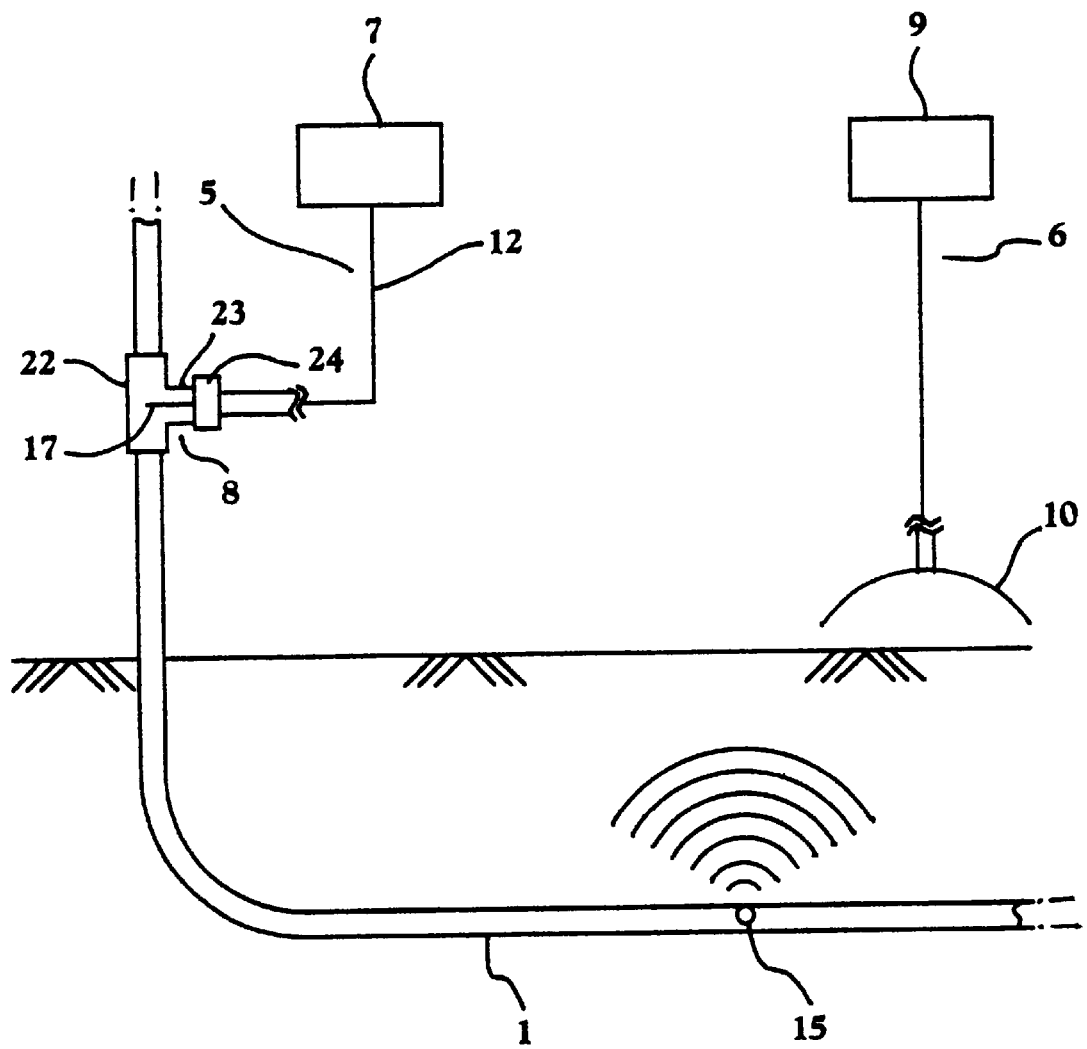
FIG. 7 is an illustration conceptually showing a method for installing an antenna in a piping system.

FIG. 7 typically shows the entire configuration where the transmitting antenna is applied to the detection of a leak point in a gas pipe.

Symbol 22 denotes a Tee pre-installed around the pipe 1, and the central branch opening 23 the Tee 22 is closed by a threaded cover 24. In this embodiment, the cover 24 is used to form a transmitting antenna section as an driving means.

FIGS. 8 through 12 concretely show embodiments of the transmitting antenna section.

Figure 8:
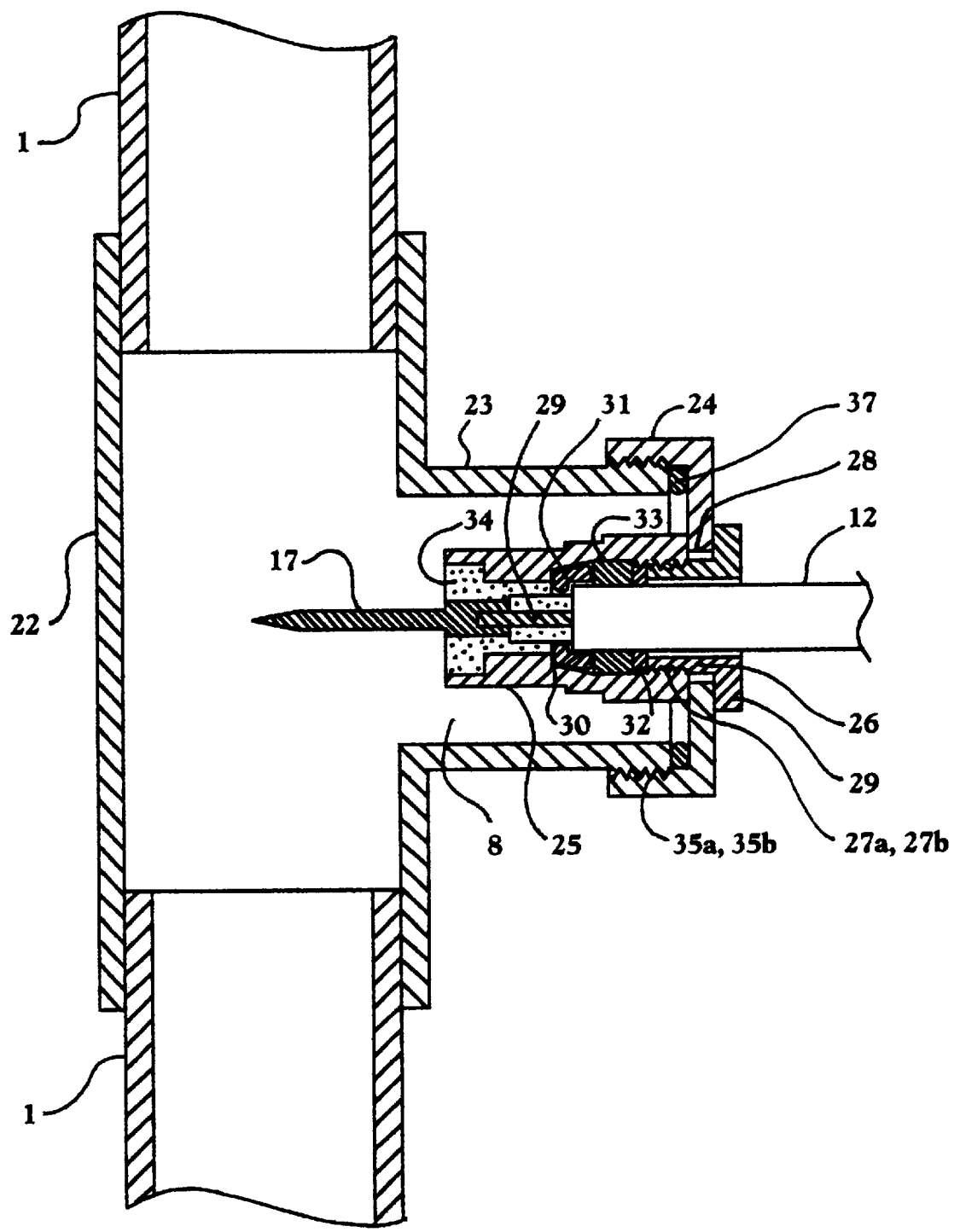
FIG. 8 is a sectional view showing a configuration of an antenna in which the installation method of FIG. 7 is applied.

In FIG. 8, symbol 25 denotes a support, and 26 denotes a lock nut. They are engaged with each other by threads 27. The threads 27a of the lock nut 26 are inserted inside from an installation hole 28 formed at the center of the cover 24 and engaged, by tightening, with the threads 27b of the support 25 arranged inside, so that the installation hole 28 of the cover 24 may be arrested by the collar 28 of the lock nut 26 and the support 25. Prior to the threaded engagement, the lock nut 26 has the tip a coaxial cable 12 inserted, to have a central lead 29 protruded, and the braid of a shielded wire 30 is spread along a clamp 31. When the threaded engagement is achieved, a washer 32 and a gasket 33 are put on, and said tightening bring the spread shielded wire 30 into pressure contact with the inner wall of the support 25 to achieve installation. On the other hand, the central lead 29 has a linearly formed probe 17 bonded at its tip, and the probe 17 is supported at the center of the support 25 by an insulator 34. In this configuration, the threads 35a of the cover 24 are engaged with the threads 35 of the central branch opening 23 of the Tee 22 by tightening, to close the opening 23. This action keeps the probe 17 in the Tee 22.

In this case, if a shielding material 37 like an O ring made of a conductive rubber or soft metal, etc. is put between the end of the opening 23 and the inside of the cover 24, when the cover 24 is tightened by engagement between the threads 35a and 35b, the shielding material 37 is kept in pressure contact with the end of the opening 23 and the inside of the cover 24, to form a shielding portion against electromagnetic waves. So, the leak of electromagnetic waves from the driving portion can be perfectly prevented. Another shielding portion can be formed by installing a shielding material at the engaging portion between the threads 35a and 35b. For example, after the threads 35b of the central branch opening 23 of the Tee 22 have had filaments made of a soft metal wound around them, or have been coated with a conductive compound, the threads 35a can be engaged with the threads 35b, to keep the deformed filaments or conductive compound in the clearance between the threads 35a and 35b, to form a shielding portion.

In this configuration, if electromagnetic waves are supplied from the transmitter proper 7 by the coaxial cable 12 to the transmitting antenna 13, the electromagnetic waves in the mode corresponding to the electric field by the probe 17 are driven in the Tee 22 and propagated from the Tee 22 to the pipe 1. Thus, the pipe 1 can propagate the electromagnetic waves in a mode similar to a circular waveguide. In the case of FIG. 8, an electromagnetic field of $TM_{01}$ mode is formed for propagation. If a damaged portion 15 such as a through hole exists in the pipe 1, the electromagnetic waves propagated in the pipe 1 leak outside from the damaged portion 15, and the leaking electromagnetic waves are received through the receiving antenna by the receiver proper 9, to detect the damaged portion 15.

Figure 9:
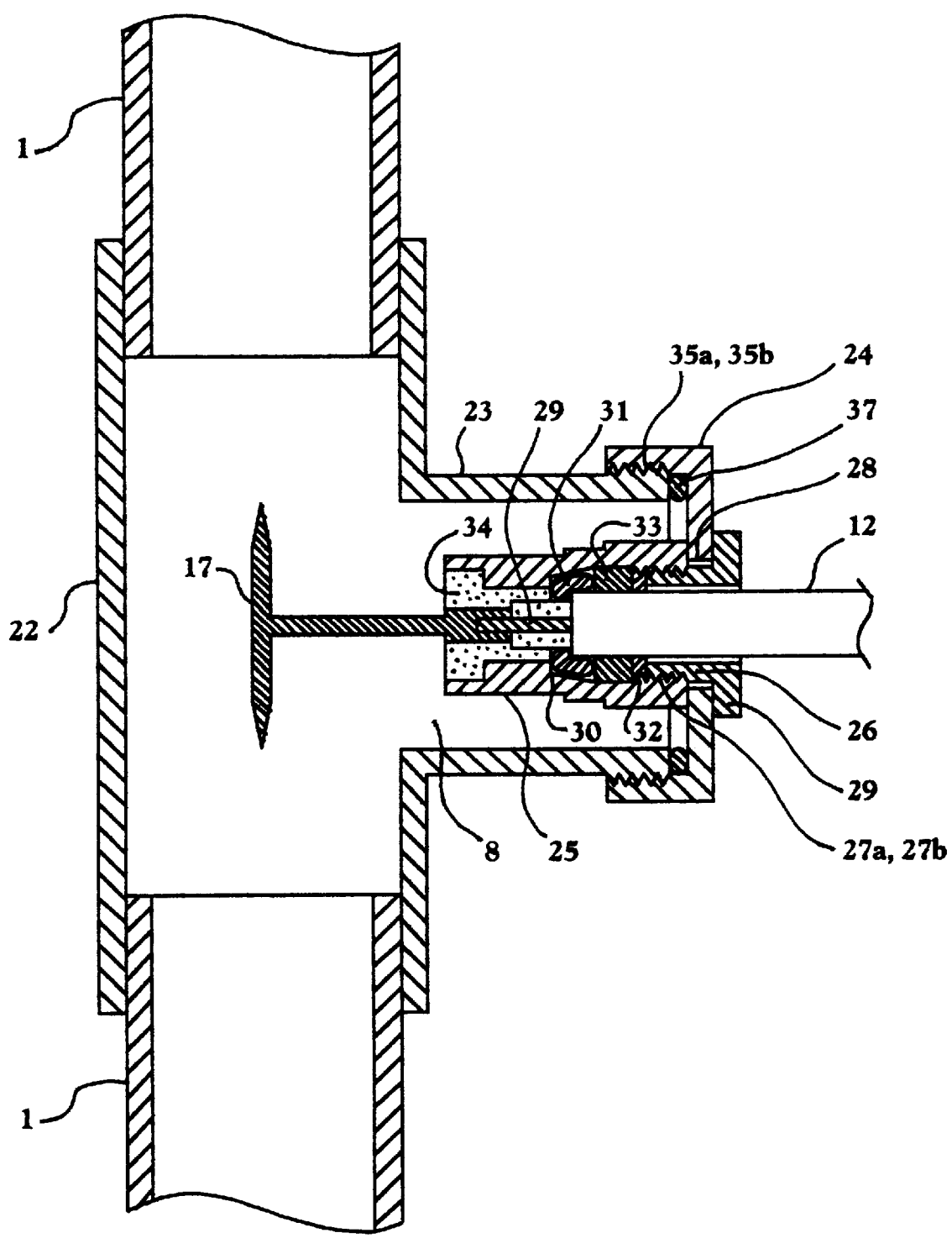
FIGS. 9 through 12 are sectional views showing other configurations of an antenna in which the installation method of FIG. 7 is applied.

FIG. 9 shows a modified example of FIG. 8. In this configuration, the probe 17 is differently formed from that of FIG. 8. The probe 17 of FIG. 9 is not simply linearly formed unlike that of FIG. 8, but is formed like T with its tips turned in the axial direction of the Tee 22. Since the other parts are identical with those of FIG. 8, they are given the same symbols for avoiding double explanation.

Figure 10:
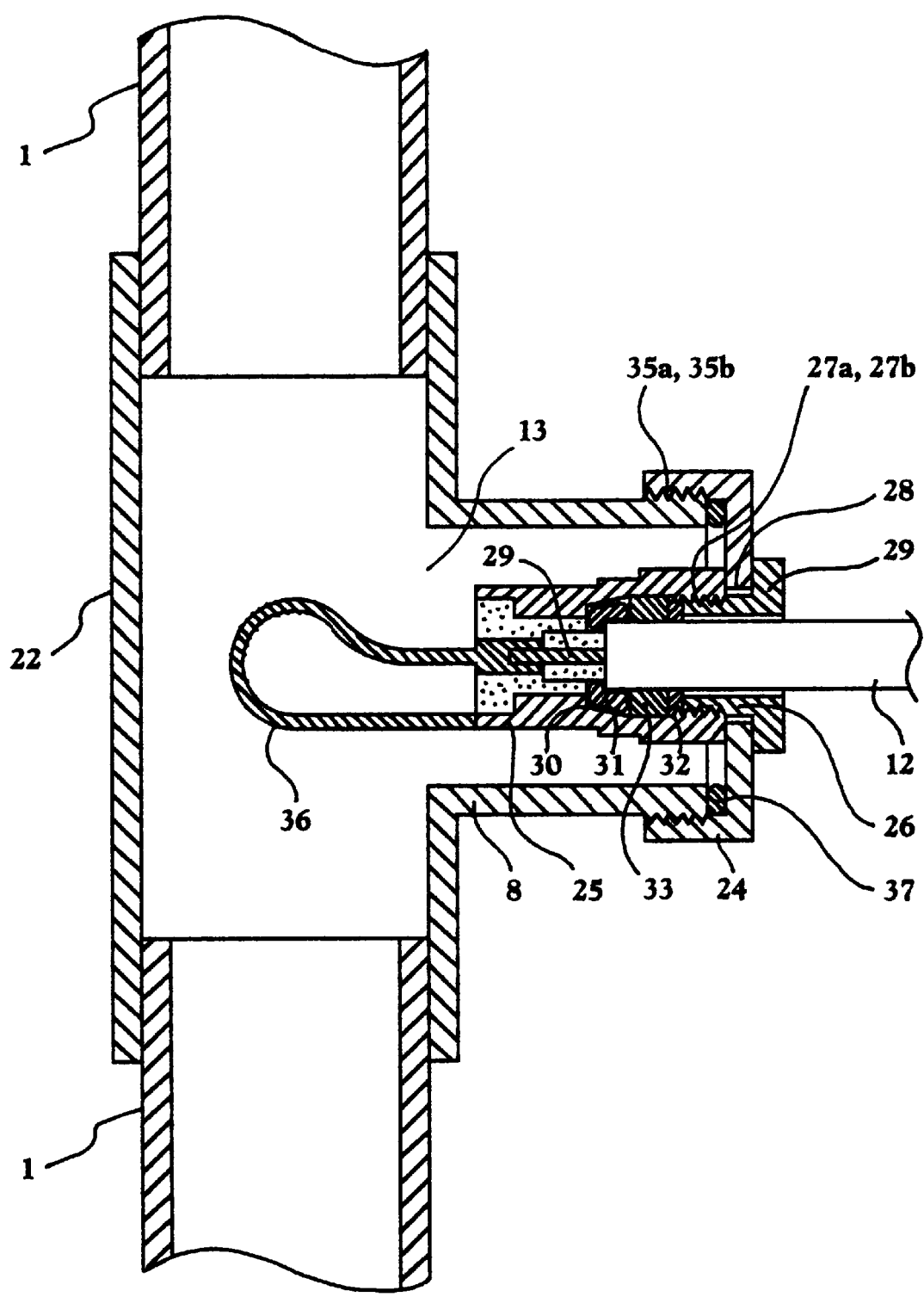

FIG. 10 shows a configuration with a loop 36 protruded inside the cover 24, instead of the probe of FIG. 8. The loop 36 is formed by connecting a conductor between the tip of the central lead 29 and the tip of the support 25. Since the other parts are identical with those of FIG. 8, they are given the same symbols for avoiding double explanation. In this embodiment, the loop 36 has its axial direction kept in the tangential direction of the inside circle of the Tee 22, and in this configuration, an electromagnetic field of $TM_{10}$ mode is formed for propagation in the pipe 1 as in FIG. 8.

Figure 11:
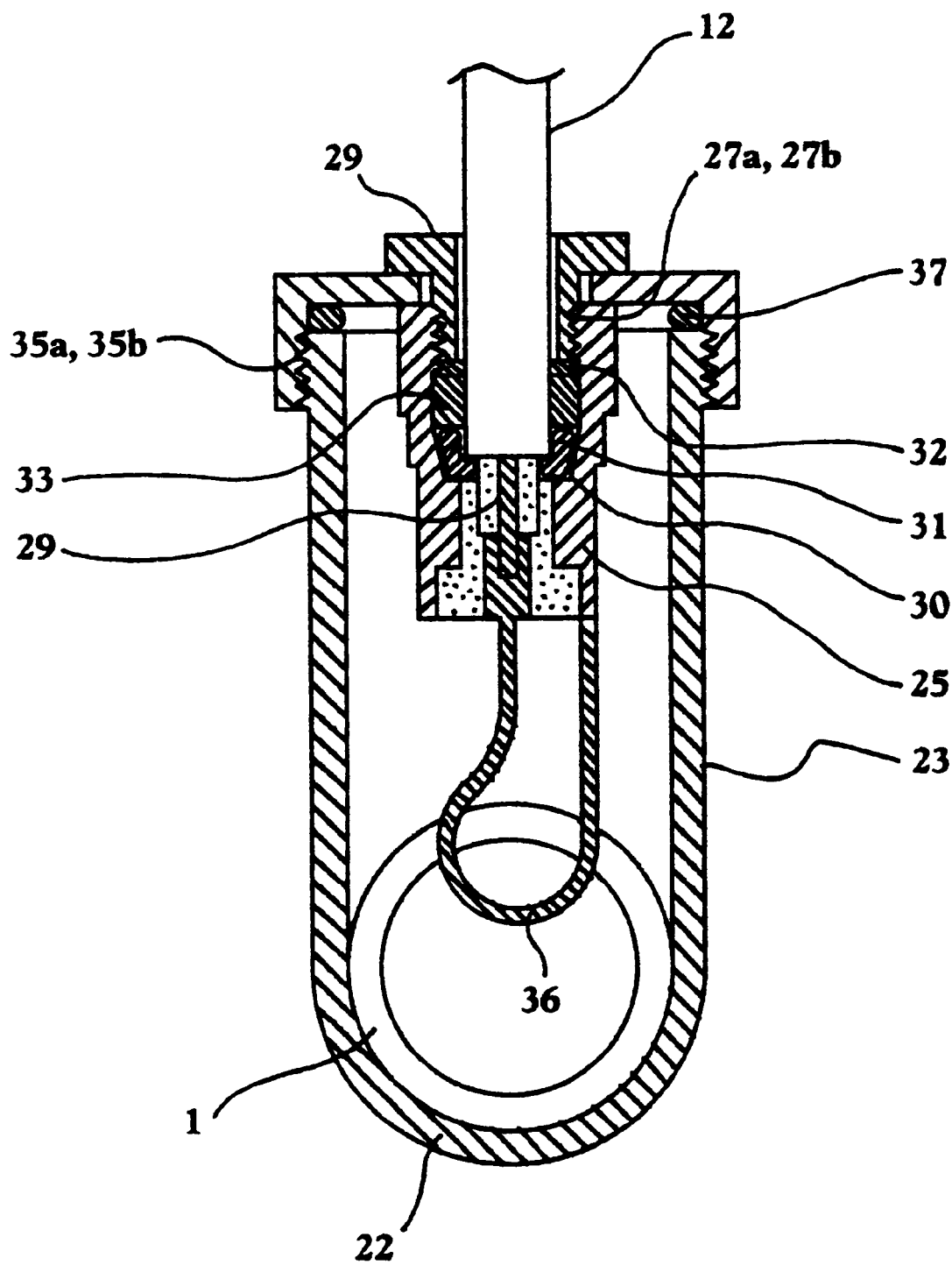

FIG. 11 is a modification example of FIG. 10. This configuration is different from that of FIG. 10 only in the direction of the axis of the loop 36. So as in the above cases, the other parts are given the same symbols for avoiding double explanation. In this embodiment, the loop 36 has its axial direction kept in the axial direction of the Tee 22, and in this configuration, an electromagnetic field of $TE_{01}$ mode is formed in the pipe 1 for propagation.

Figure 12:
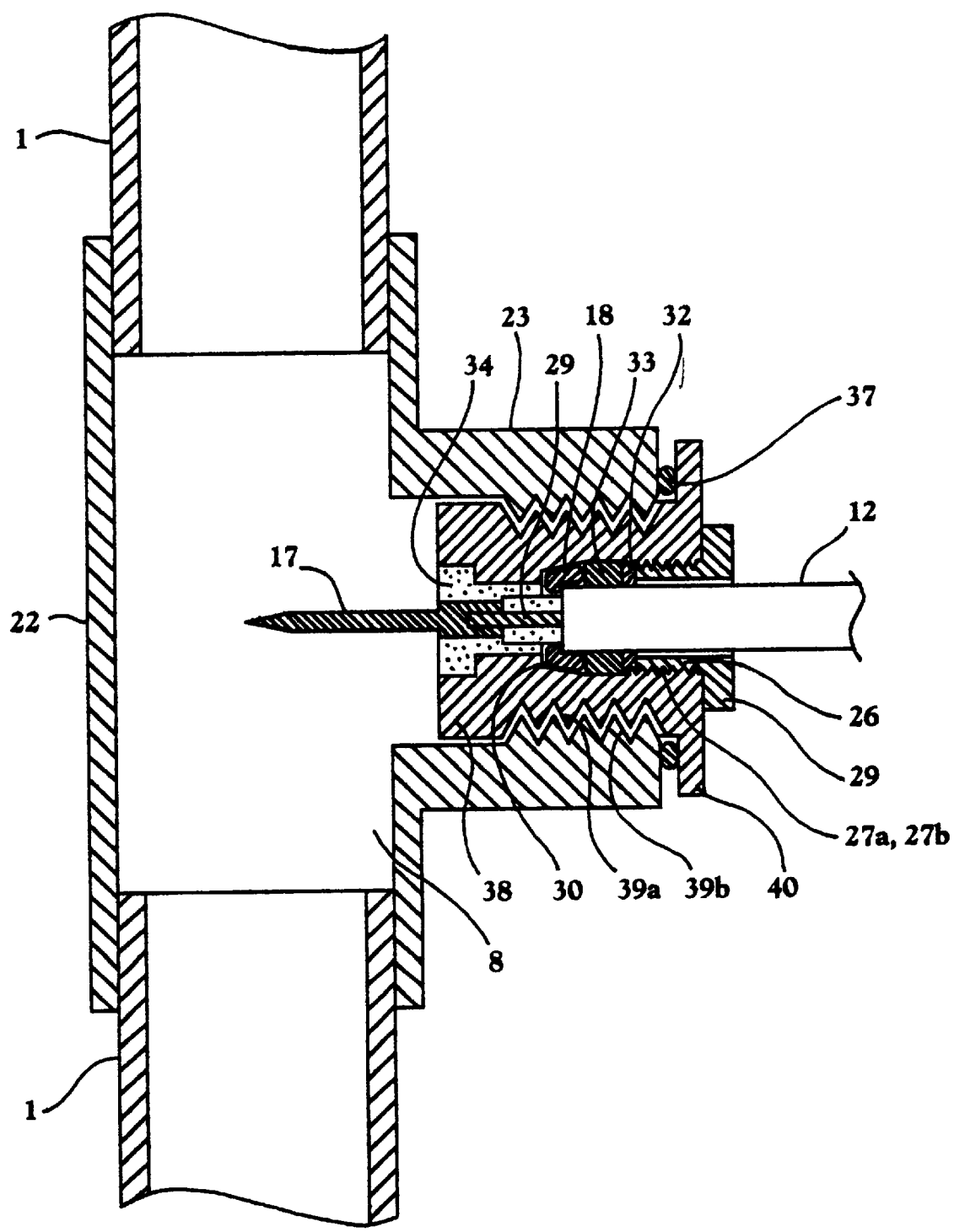

FIG. 12 is a modification example of FIG. 8. In this configuration, unlike the above configurations, the cover 24 is threadedly engaged with the inside of the opening 23. Symbol 38 is a support corresponding to the support 25 of FIG. 1, and the support 38 has threads 39a formed around it which are engaged with the threads 39b formed inside the central branch opening of the Tee 22. The support 38 also has a collar 40 at one end. The other parts are the same as in FIG. 8 and are given the same symbols to avoid double explanation.

The mechanism for supporting the coaxial cable 12 by the cover 24, the structure of the probe 17 and the loop 36 at the tip of the coaxial cable 12, the mechanism for supporting the probe and the loop 36, etc. can be those as adopted in the conventional coaxial waveguide transducers, etc.

In the above embodiments of the transmitting antenna 13, since electromagnetic waves are driven from the Tee 22 installed on the extension of the pipe 1 into the pipe 1, it is not necessary to cut off at one end of the pipe for excitation, and therefore it is not necessary to stop gas supply if any of the above embodiments is applied to the piping system for a city gas supply network. Furthermore, the leak of electromagnetic waves from the Tee 22 as an driving section can be reliably prevented.

In the inspection method described above, electromagnetic waves are driven from the transmitting antenna 13 of the transmitter 5 into the pipe 1 for propagation, and the electromagnetic waves leaking from the damaged portion 15 are received by the receiver 6 through the receiving antenna moved along the pipe 1 outside the pipe 10. Contrary to this method, it is also possible to move the transmitting antenna 13 of the transmitter along the pipe 1 outside the piping system to be inspected, while transmitting electromagnetic waves toward the pipe 1 from outside the piping system, for receiving them by the receiving antenna 10 of the transmitter 6 installed at a proper place of the pipe 1, even though this method is not illustrated in the drawings.

According to this method, the electromagnetic waves transmitted from outside enter the piping system through the damaged portion 15, and are propagated in the pipe 1, to be received by the receiver through the receiving antenna, to allow the existence of the damaged portion to be detected. Since the level of the electromagnetic waves entering from the damaged portion and received by the receiver is highest at a location where the transmitting antenna is nearest to the damaged portion, the location of the damaged portion in the piping system can be accurately detected as the location of the antenna at which the level of electromagnetic waves received becomes a peak.

In this method, the transmitter and the receiver can be composed in any way as described before, and the receiving antenna can be selected from those examples of the transmitting antenna described above.

In the above method, the receiving antenna can be moved in relation with the movement of the transmitting antenna, without being fixed in the pipe, to receive the electromagnetic waves entering the piping system from outside, for inspection of elements of the piping system. In this case, in addition to the location of the transmitting antenna at which the level of electromagnetic waves received becomes a peak, the location of the receiving antenna can also be taken into account for accurately detecting the damaged portion 15.

In the above description, the portions where electromagnetic waves leak, i.e., the portions examined for identification of location are damaged portions 15 such as holes formed by corrosion and cracks in the pipe. However, joints of a piping system can also be detected.

Figure 13:
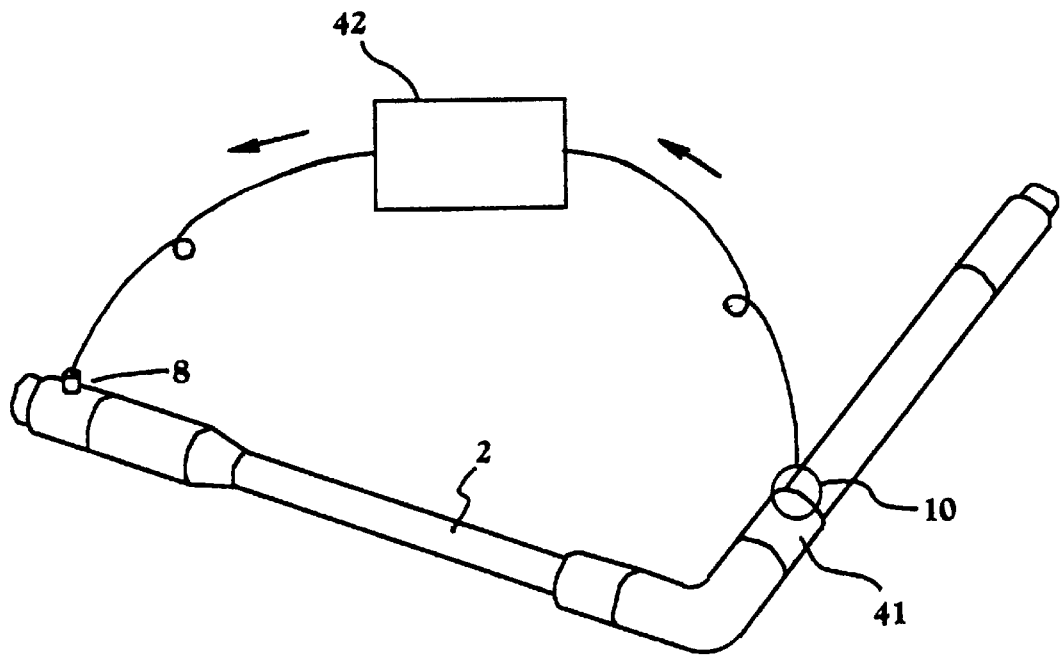
FIG. 13 is an illustration conceptually showing a tester for inspecting the leak of electromagnetic waves through a joint.

FIG. 13 shows a system for measuring the leak of electromagnetic waves from a joint 41 in a piping system with joints. Symbol 42 is a network analyzer which drives electromagnetic waves on the transmission side and measures the level of electromagnetic waves received with the receiving antenna 10 on the receiving side located near the joint 41. A piping system has pipe line sections of 40 mm in minimum diameter, and in these sections, and the cut-off frequency of electromagnetic waves in these sections is about 4.3 GHz.

Figure 14:
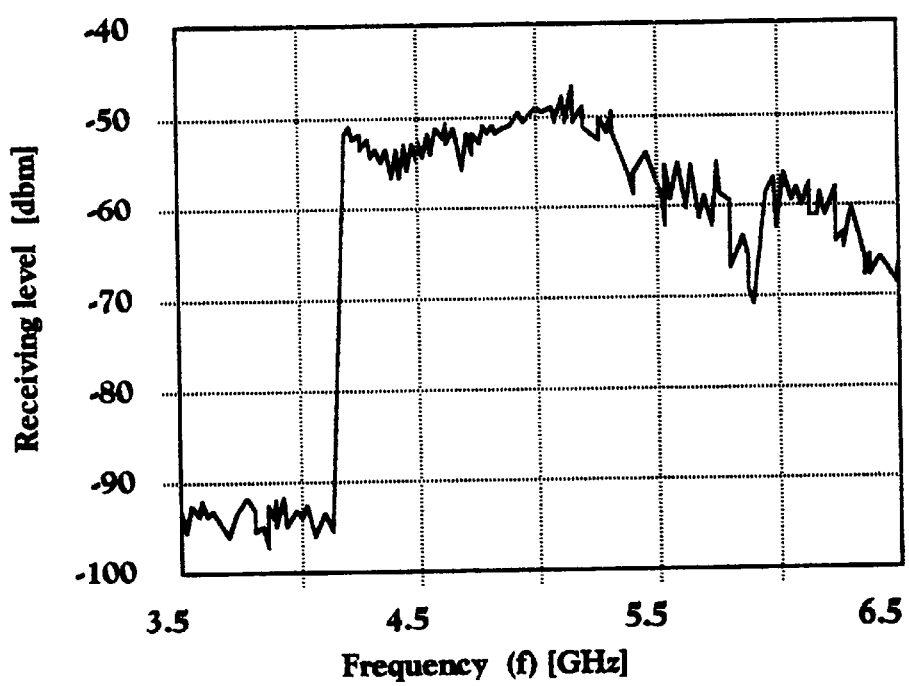
FIG. 14 is a graph showing the results of a test in FIG. 13.

FIG. 14 shows the results of measurement. It can be seen that at higher than about 4.3 GHz close to the above cut-off frequency, electromagnetic waves leak from a joint.

If the above inspection method is applied to a piping system with joints, electromagnetic waves leak through a rubber ring or gasket when the joint is a mechanical joint, or through a gasket if a flange joint, or through a non-conductive member such as a shielding material if a screw joint.

In this case, since electromagnetic waves are propagated for a relatively long distance in a pipe to leak slightly at every joint, the excitation of electromagnetic waves at one place allows the detection of continual plural joints, and in reference to each peak in the level of electromagnetic waves received by the receiver, the location of the joint can be detected. In this case, if the receiving antenna is sharply directional, it can be moved along the pipe 1 (the route in which the pipe 1 is estimated to be buried in reference to any information material such as drawing), while the direction is properly changed to detect a peak, the location of the joint can be accurately detected in reference to the direction of the receiving antenna corresponding to the peak, and the influence of external noise can be minimized. However, if the receiving antenna used is non-directional or weakly directional, it can be moved along the pipe, and the location at which the level of electromagnetic waves received becomes a peak can be detected as the location right above the joint.

On the other hand, since the quantity of leaking electromagnetic waves increases if the joint is loosely tightened, the looseness of a joint can also be detected in reference to the level of electromagnetic waves received. At a particular joint, if the receiving conditions such as the distance from the receiving antenna, direction, etc. are the same, the level of electromagnetic waves leaking from the joint and received depends on the looseness. So, if the level measured is compared with the data of the levels measured in the past and found to be the same, the joint can be estimated to be sound, and if larger, the joint can be estimated to be loose.

To estimate the looseness of a joint of a metallic pipe in reference to the level of electromagnetic waves received, it is necessary that the receiving conditions are the same as described above, and if the pipe is metallic, it is of course necessary that such conditions as the distance from the receiving antenna, direction, etc. are the same and also that the characteristics of surroundings of the pipe buried underground or installed in a wall for electromagnetic waves are constant. Unless these conditions are satisfied, it is difficult to estimate the looseness of a joint in reference to the level of electromagnetic waves received. However, even if the pipe is buried, the looseness can be estimated when all the above conditions are satisfied, and in the case of an exposed pipe for which receiving conditions can be easily made the same, the estimation is possible.

In the above inspection of joints, as described before, the transmitting antenna can also be arranged outside the pipe while the receiving antenna can be arranged inside the pipe for detecting the electromagnetic waves entering through the joints from outside, needless to say.

In the embodiment of the present invention described below, the location of a leak portion such as a damaged portion like a corrosion hole or joint of a pipe not exposed can be detected, and in addition, the distance from a properly set reference location of the pipe to the detected leak portion can be measured.

Figure 15:
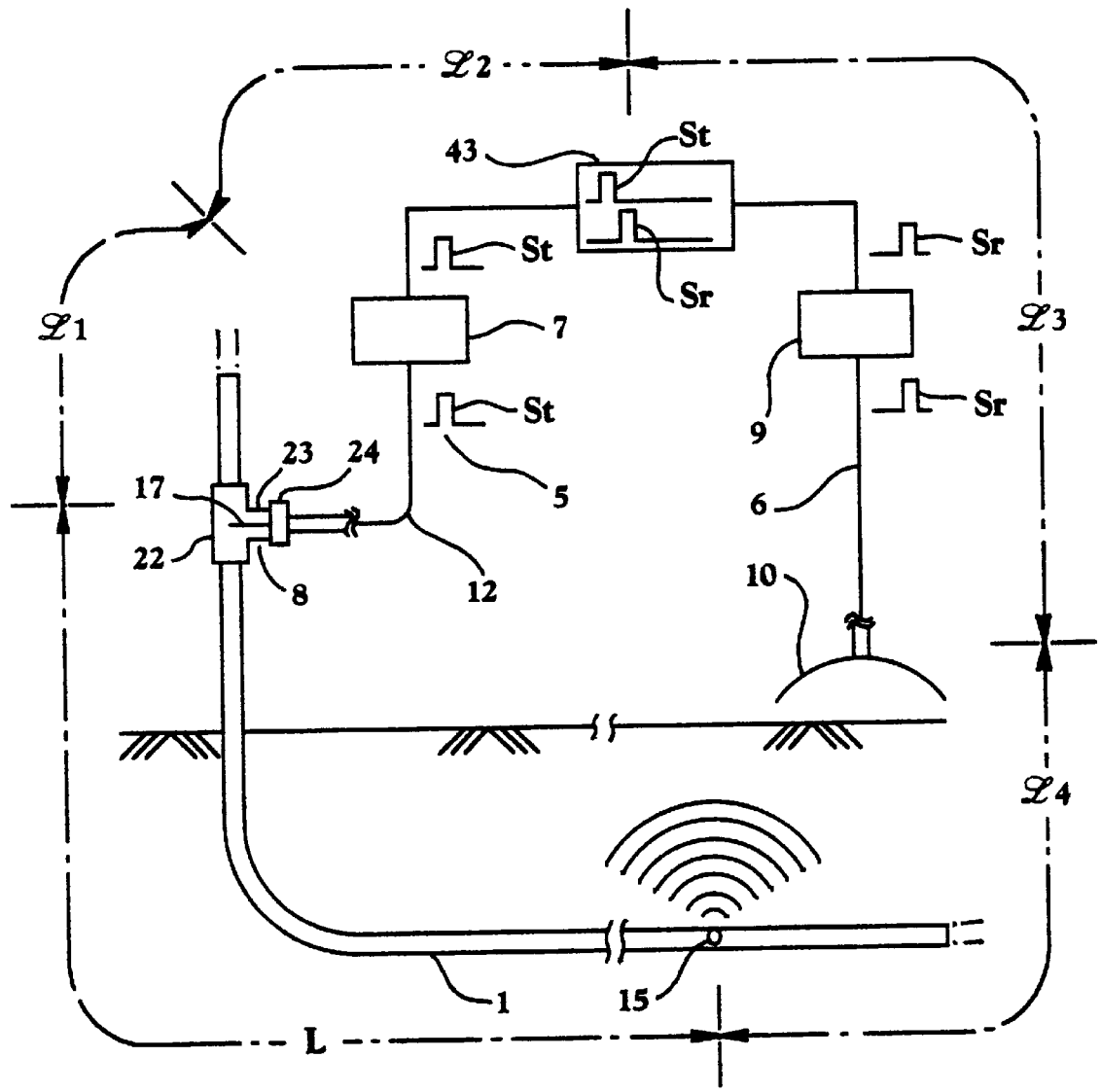
FIG. 15 is an illustration conceptually showing the action of distance measurement in a piping system.

The embodiment is shown as a conceptual view in FIG. 15.

Symbol 1 denotes a pipe to be inspected. In this example, as in FIG. 7, the transmitting antenna 8 as an driving section is installed in the cover 24 of the central branch opening 23 of the Tee, to protrude the probe 17 or loop (not illustrated) into the Tee 22. Symbol 43 denotes a processor, and the other parts are the same as in FIG. 7 and are given the same symbols to avoid double explanation.

In this configuration, on the transmitter 5 side, the transmitting antenna 8 drives electromagnetic waves in the pipe 1, and in this state, a worker on the receiver 6 side moves the antenna 10, to find the electromagnetic waves leaking from the damaged portion 15 of the pipe 1. If the electromagnetic waves leaking from the damaged portion 15 such as a hole formed by corrosion in the pipe 1 are received, the location of the damaged portion 15 can be detected on the ground. If the antenna 10 used is non-directional or weakly directional, the antenna 10 can be moved along the pipe 1 (the route where the pipe 1 is estimated to be buried based on any information material such as drawing), and the location where the level of electromagnetic waves received becomes a peak can be detected as the location right above the damaged portion 15. When the antenna 10 used is sharply directional, the location right above the damaged portion can be detected at a high resolution, and the influence by external noise is also minimized.

As described above, symbol 43 denotes a processor, and the processor 43 compares the electromagnetic waves transmitted by the transmitter 5 and the electromagnetic waves detected by the receiver 6, to obtain the propagation time of electromagnetic waves, and distance from the driving place, i.e., the transmitting antenna 8 installed at the open end of the pipe 1 to the damaged portion 15 where leak was detected by the receiver 6.

To obtain the propagation time by comparing the electromagnetic waves transmitted by the transmitter S with the electromagnetic waves detected by the receiver 6, the transmitted electromagnetic waves are modulated. The electromagnetic waves can be modulated by any of various modulation methods such as pulse modulation, amplitude modulation, frequency modulation or code modulation, and the time difference between the modulated and transmitted electromagnetic waves and the received electromagnetic waves can be measured or any proper known method such as direct measurement, detection of phase difference or detection of deviation in the coefficient of correlation. In this case, the pulse compression method used for improving S/N, etc. in radar and ultrasonic measurement can be applied, and the transmitted electromagnetic waves are modulated by linear FM (chirp waves), barker code, M series code, complementary series code, etc.

In this configuration, the processor 43 commands to feed a signal St modulated as predetermined from the transmitter proper 7 through the coaxial cable 12 to the transmitting antenna 8, for driving electromagnetic waves in the pipe 1 for propagation. Simultaneously, the signal St similar to the driven electromagnetic waves is delivered to the processor 43 for comparison with the received signal. On the other hand, the signal Sr of electromagnetic waves leaking from the damaged portion 15 of the pipe and received by the receiver 6 is pre-processed to be amplified, etc. as required, and delivered to the processor 43 for comparison with the transmitted signal.

The processor 43 compares the transmitted signal St with the received signal Sr, and measures the time difference. The time difference can be measured by using any of proper methods stated above suitable for the modulation method adopted. For example, in the case of pulse modulation, the time difference between pulses can be directionally measured, and in the case of amplitude modulation, the phase difference between the modulated transmitted signal St and the modulated received signal Sr can be measured for calculating the time difference. For code modulation or any other proper modulation, the deviation in the coefficient of correlation can be detected to calculate the time difference.

The time difference between the transmitted signal St and the received signal Sr thus obtained includes the propagation time of electromagnetic waves corresponding to the route L from the transmitting antenna 8 to the damaged portion 15 such as a hole formed by corrosion, the propagation time corresponding to the route $l_1$ from the transmitter proper 7 to the transmitting antenna 8, the propagation time corresponding to the route $l_2$ from the transmitter proper 7 to the processor 43, the propagation time corresponding to the route $l_3$ from the antenna 10 through the receiver proper 9 to the processor 43, and the propagation time corresponding to the route $l_4$ from the damaged portion $l_5$ to the antenna 10. Therefore, the time difference obtained is not the propagation time of electromagnetic waves corresponding to the route L from the transmitting antenna 8 to the damaged portion 15.

However, the propagation time of electromagnetic waves corresponding to the routes $l_1$, $l_2$ and $l_3$ do not change, and can be measured beforehand, and the distance of the route $l_4$ is the sum of the buried depth of the pipe 1 and the height from the ground surface to the antenna 10. So, the former can be known in reference to the piping work diagram, etc., and the latter can be obtained by measurement. Therefore, the propagation time of electromagnetic waves corresponding to the route L from the transmitting antenna 8 to the damaged portion 15 can be obtained by subtracting the propagation times of electromagnetic waves corresponding to the routes $l_1$, $l_2$, $l_3$ and $l_4$ from the time difference obtained by the above measurement.

In this way, the propagation time of electromagnetic waves corresponding to the route L from the transmitting antenna 8 to the damaged portion 15 can be obtained, and therefore, the distance of the route L can be calculated.

As described above, the location of the damaged portion such as a hole formed by corrosion in the pipe 1 can be detected on the ground by detecting the electromagnetic waves leaking from the damaged portion 15, and the distance of the pipe 1 from the transmitting antenna 8 to the damaged portion 15 can be obtained by comparing the electromagnetic waves received by the transmitter 6 with the electromagnetic waves received by the receiver S as modulated signals, to measure the time difference, and measuring the propagation time of electromagnetic waves from the transmitting antenna 8 to the damaged portion 15 from the time difference, etc. Therefore, the damaged portion 15 such as a hole formed by corrosion can be efficiently repaired, for example, by closing it by a resin, etc. using a pig, etc. from inside the pipe 1.

Figure 16:
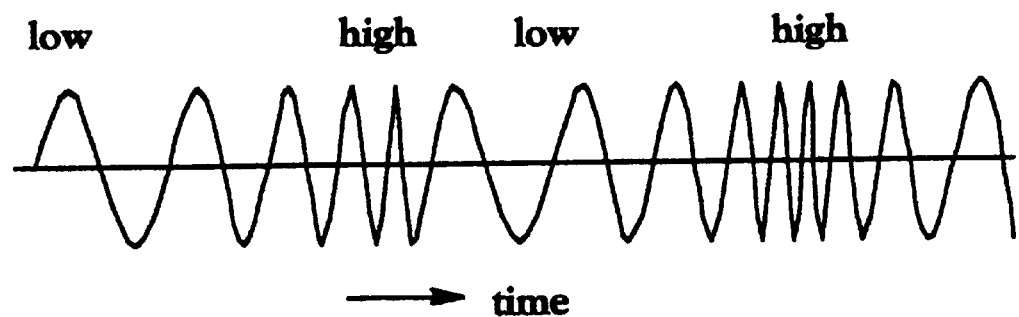
FIGS. 16 through 18 show waveforms of electromagnetic waves transmitted from a transmitting antenna.
Figure 17:
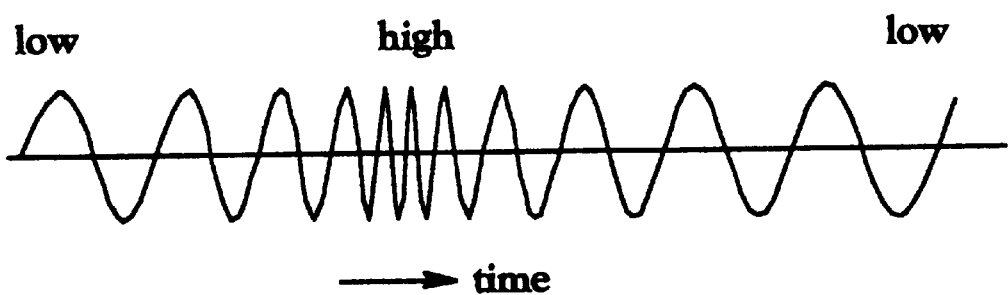
Figure 18:
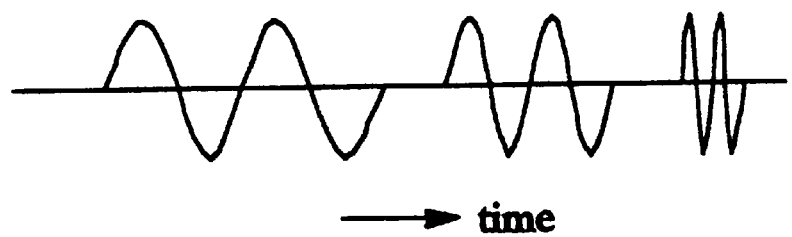

The following embodiment corresponds to FIGS. 16 to 18. In the inspection method for driving electromagnetic waves in a pipe with a transmitting antenna installed at a proper place in the pipe, or on the contrary, in the inspection method for receiving the electromagnetic waves propagated in a pipe with a receiving antenna installed at a proper place in the pipe, the driven electromagnetic waves are changed over time not to form a fixed electromagnetic field distribution in the pipe.

For this purpose, the transmitter is provided with a means for changing the frequency of driven electromagnetic waves over time in addition to the basic components required for driving electromagnetic waves such as an oscillator and amplifier. FIGS. 16 to 18 typically show examples of frequency change over time. In FIGS. 16 and 17, the frequency is continuously changed by sweep in a certain range. In FIG. 16, the frequency is changed as low→high, high→low, low→high, . . . In FIG. 17, the frequency is changed as low→high, low→high, low→high, . . . As a means to obtain such frequency change over time, a sweep oscillator can be used as the oscillator of the transmitter. In FIG. 18, the frequency is changed in steps, and a means for obtaining such frequency change over time, a programmable oscillator which allows plural oscillation frequencies to be set can be used as the oscillator of the transmitter.

In general, if electromagnetic waves are driven and propagated in the pipe by the transmitter, magnetic field components in the pipe wall direction and electric field components in the direction perpendicular to the pipe wall cause the leak of electromagnetic waves at a damaged portion such as a hole formed by corrosion or a joint, etc. in the pipe, and the leaking electromagnetic waves are received by the receiver through the receiving antenna, to detect the damaged portion. However, electromagnetic waves of a certain frequency at a point of time may not form the above mentioned electric and magnetic field components at the certain frequency, and at the point of time, leakage of electromagnetic fields is hard to occur. Therefore, if the electromagnetic waves of such a frequency are continuously driven, it is difficult to detect a damaged portion of a pipe in reference to the leaking electromagnetic waves.

However, in the configuration described above, since the frequency of electromagnetic waves driven in the pipe are changed over time, even if electric and magnetic field components hard to cause the leak from a damaged portion at a certain frequency at a point of time, the electromagnetic field distribution is changed at a different frequency at the next point of time, to cause electromagnetic waves to leak from the damaged portion, for allowing the detection of the damaged portion.

Figure 19:
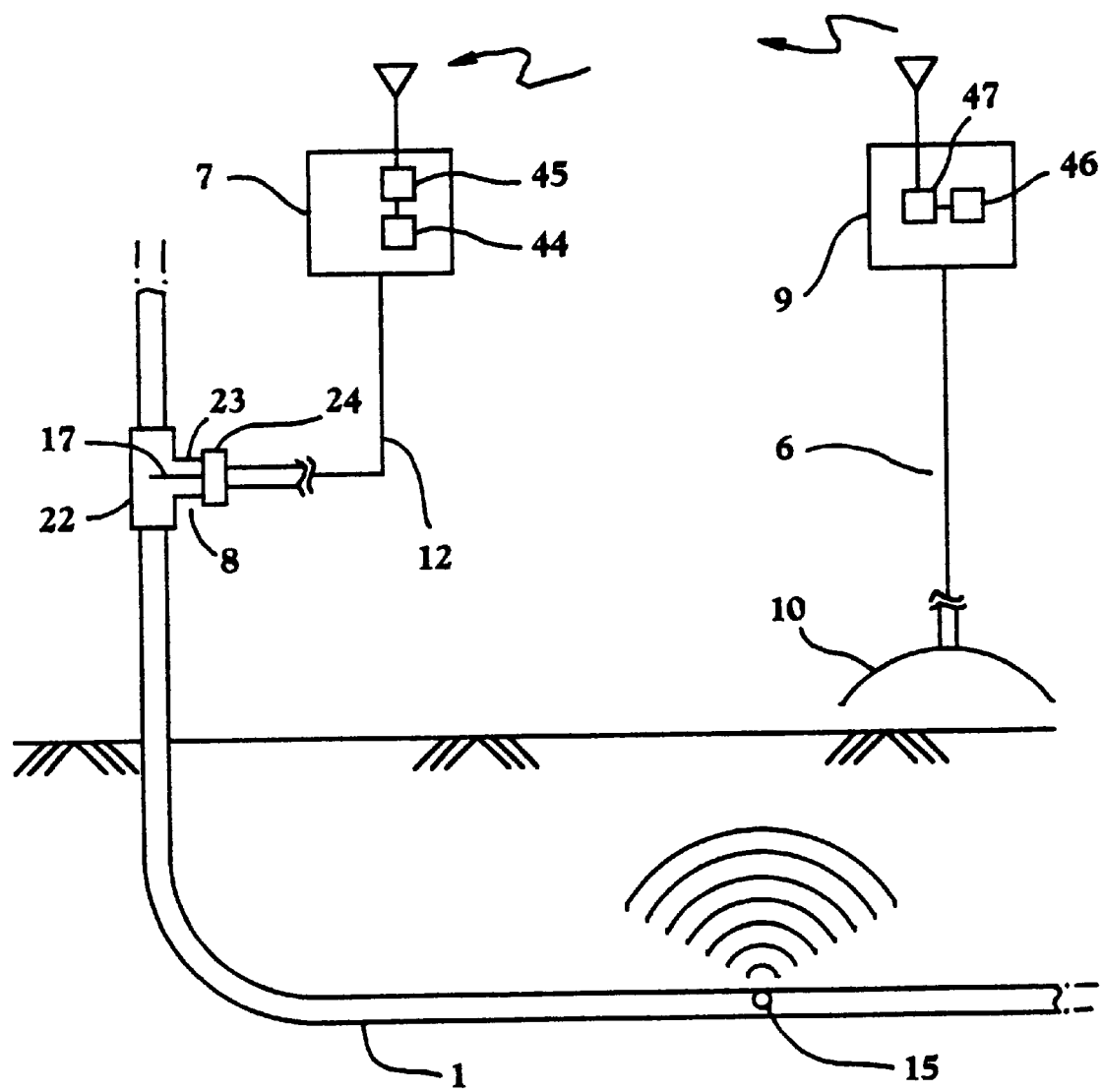
FIG. 19 is an illustration conceptually showing a pipe inspection action with the transmission of electromagnetic waves turned on and off.
Figure 20:
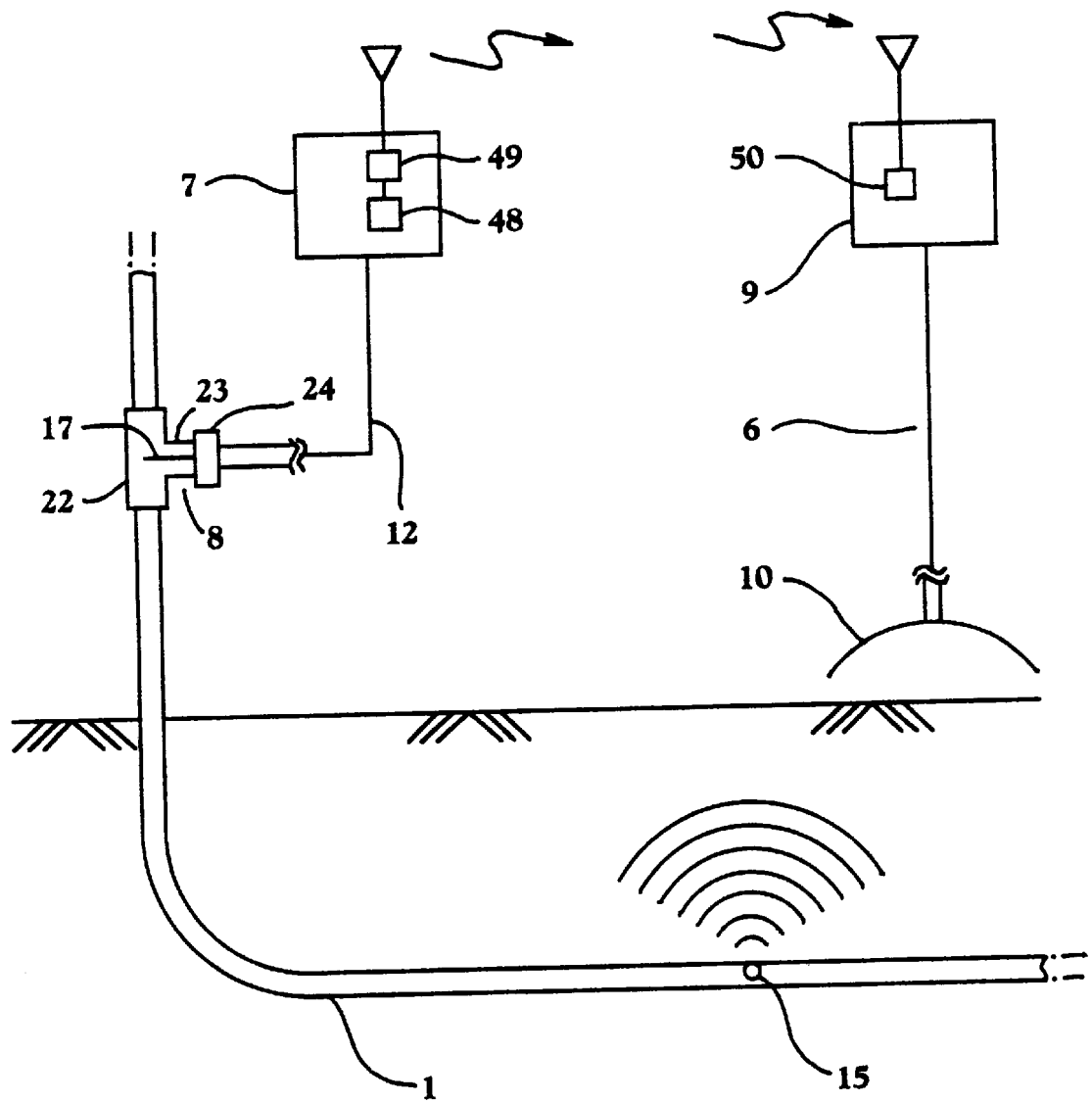
FIG. 20 is an illustration conceptually showing another pipe inspection action with the transmission of electromagnetic waves turned on and off.
Figure 21A:
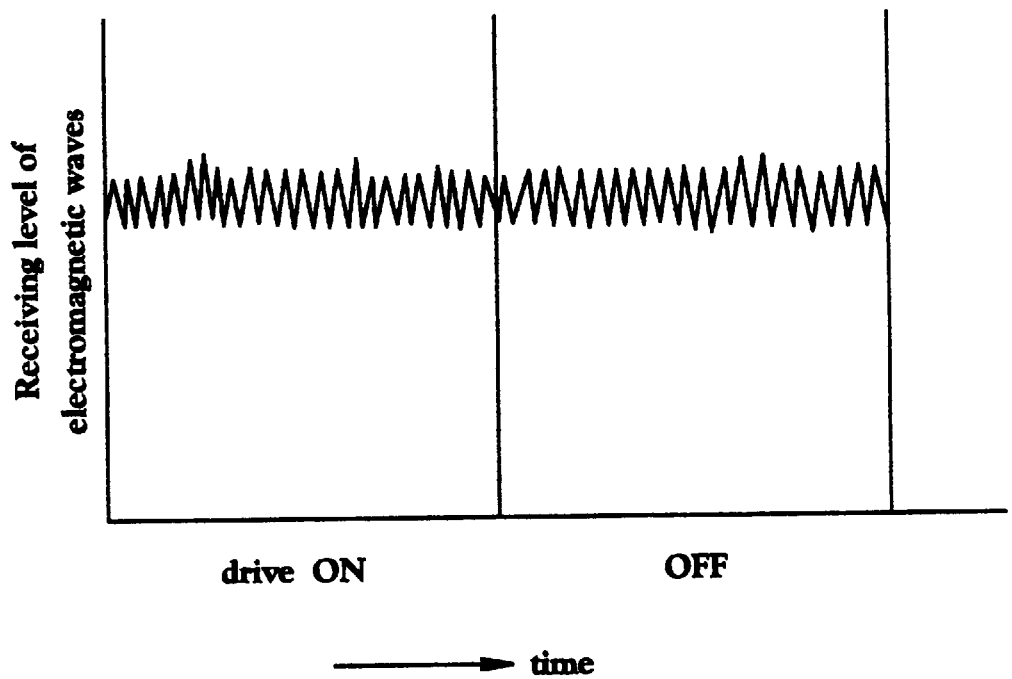
FIG. 21 is an illustration conceptually showing the results of inspection actions of FIGS. 19 and 20.
Figure 21B:
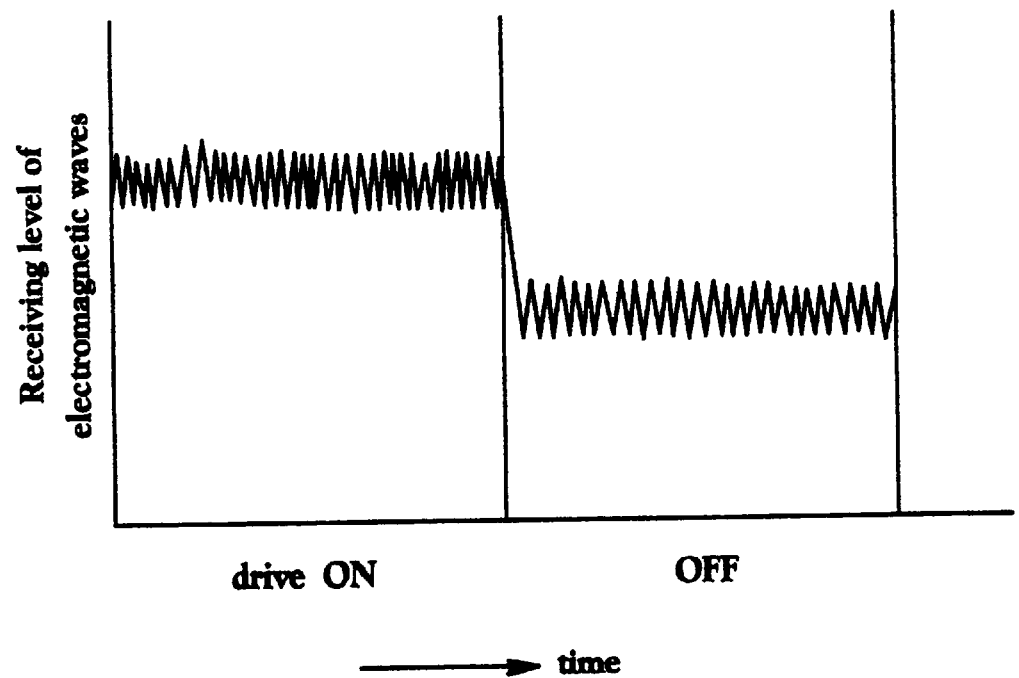

The following embodiment corresponds to FIGS. 19 to 21, and relates to a method of detecting leaking electromagnetic waves by letting the receiving antenna move along a pipe outside a piping system. In this inspection method, when electromagnetic waves are received by the receiver, whether they include those leaking from a leak portion or external noise only can be easily and reliably identified, and therefore, the error detection of the leak portion can be prevented.

In this method, the transmitter proper 7 is provided with a drive ON-OFF control means 44 and a receiving means 45 for receiving the control signal of the ON-OFF control means. The ON-OFF control means 44 can be composed to turn on and off the oscillator or turn on and off the wave guiding channel or in any other proper way. On the other hand, the receiver proper 9 is provided with a remote control switch for turning on and off the ON-OFF control means 44 of the transmitter proper 7, in addition to the basic components required for receiving electromagnetic waves such as a detector, amplifier, signal processor, and received signal level indicator, and the remote control switch is composed of a control switch 46 and a switch state transmitting means 47. The transmitting means 47 and the receiving means 45 are expressed as wireless communication means in the drawings, but they can also be wired communication means, needless to say.

In this configuration, the worker on the transmitter proper 7 side installs the transmitting antenna 8 to the Tee 22 provided on the extension of, for example, a gas pipe 1 to be inspected for identification of damaged portions such as leak portions, and connect the transmitting antenna 8 with the transmitter proper 7 for actuating it. The worker on the receiver proper 9 side operates the control switch 46, and sends an ON command from the transmitting means 47 to the ON-OFF control means 44 through the receiving means 45 of the transmitter proper 7, to turn on the drive of electromagnetic waves in the transmitting antenna 8. The worker moves the receiving antenna 10 to search for electromagnetic waves, watching the level of electromagnetic waves received and indicated on the indicator of the receiver proper 9.

In this search, when a portion where the indicated level becomes high is detected, the worker operates the control switch 46, to send an OFF command to the ON-OFF control means of the transmitter proper 7, to turn off the drive of electromagnetic waves in the transmitting antenna 8. In this case, if the electromagnetic waves received in ON state contain the electromagnetic waves leaking from the damaged portion 15 of the pipe 1, the indicated level declines as shown in FIG. 21 (*b*) when the drive is turned off. On the other hand, when the electromagnetic waves received in ON state do not contain the electromagnetic waves leaking from the damaged portion 15 of the pipe and are external noise only, the indicated level does not change as shown in FIG. 21 (*a*) even if the drive is turned off. Therefore, if the indicated level in OFF state is compared with the indicated level in ON state, the leaking electromagnetic waves can be identified, and the damaged portion can be detected in reference to the leaking electromagnetic waves. The comparison between OFF state and ON state in indicated level can be done by a worker or can also be automated.

FIG. 20 typically shows another configuration to which the method of the present invention is applied. The same components as in FIG. 19 are given the same symbols to avoid double explanation.

In this example, the transmitter proper 7 is provided with an ON-OFF control means to turn on and off the drive of electromagnetic waves by itself, and a transmitting means 49 for the signals synchronous with the ON and OFF actions. On the other hand, the receiver proper 9 is provided with a receiving means 50 for receiving the signals synchronous with the ON and OFF actions, to indicate the action state.

In the configuration of FIG. 29, on the transmitter proper 7 side, the drive is turned on and off at time intervals preset in a memory means, etc., and on the receiver proper 9 side, the synchronous signal transmitted from the transmitter proper 7 side is received, to indicate the ON or OFF state of drive. Therefore, when the worker on the receiver proper 9 side detects a location where the indicated level is high during his search, as in the case of FIG. 19 in reference to the ON and OFF states of drive and the indicated level, he can detect whether the electromagnetic waves received contain the electromagnetic waves leaking from the damaged portion 15 of the pipe 1, by comparing the indicated level in OFF state and the indicated level in ON state.

In the respective methods described above, the electromagnetic waves transmitted from the transmitter are propagated in the pipe concerned of a piping system at a frequency higher than the cut-off frequency for the pipe used as a wave guiding channel of electromagnetic waves, but in the following two embodiments, the frequency is kept lower than the cut-off frequency.

Figure 22:
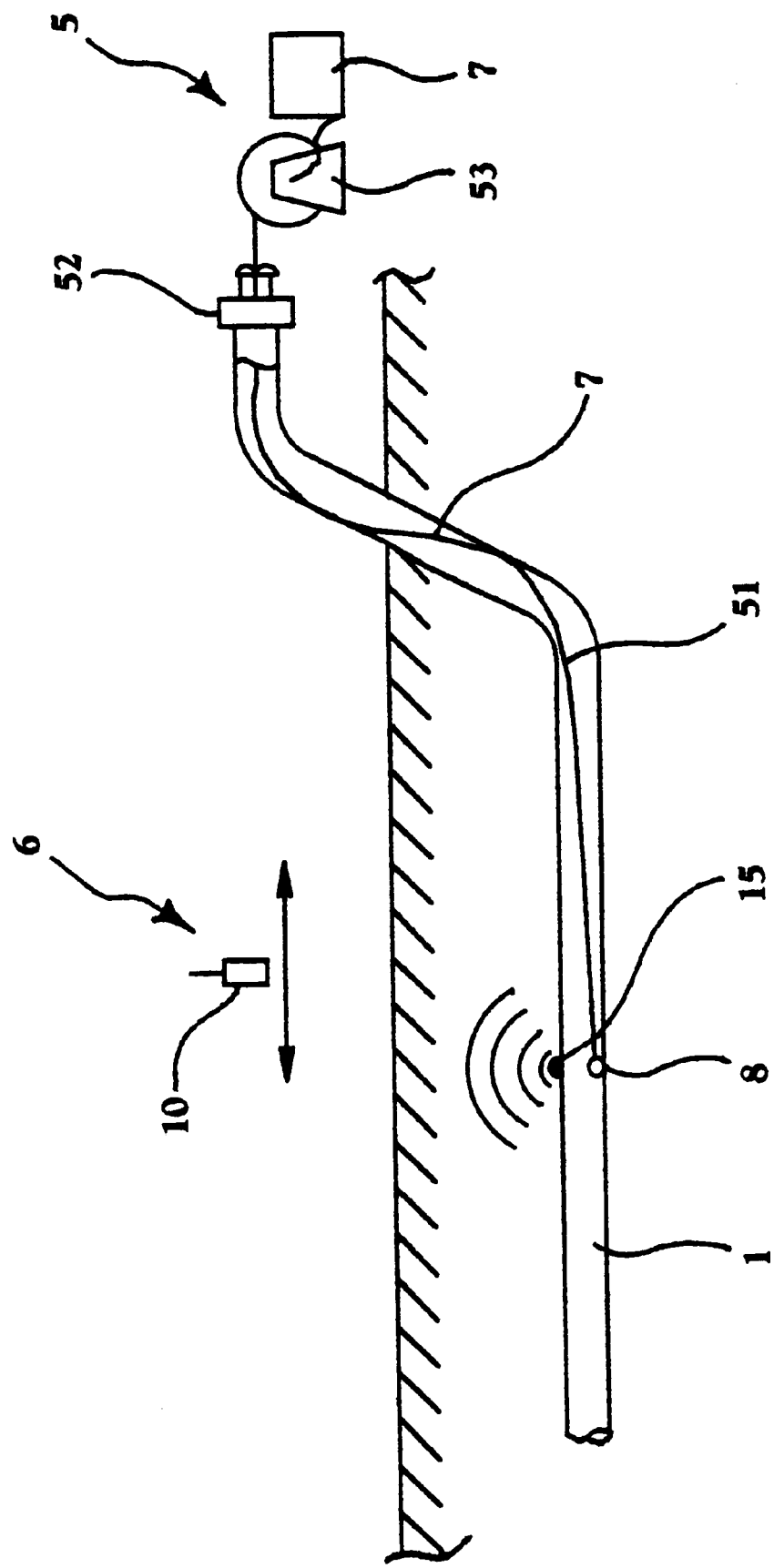
FIG. 22 is an illustration conceptually showing an inspection action with an antenna moved.
Figure 23:
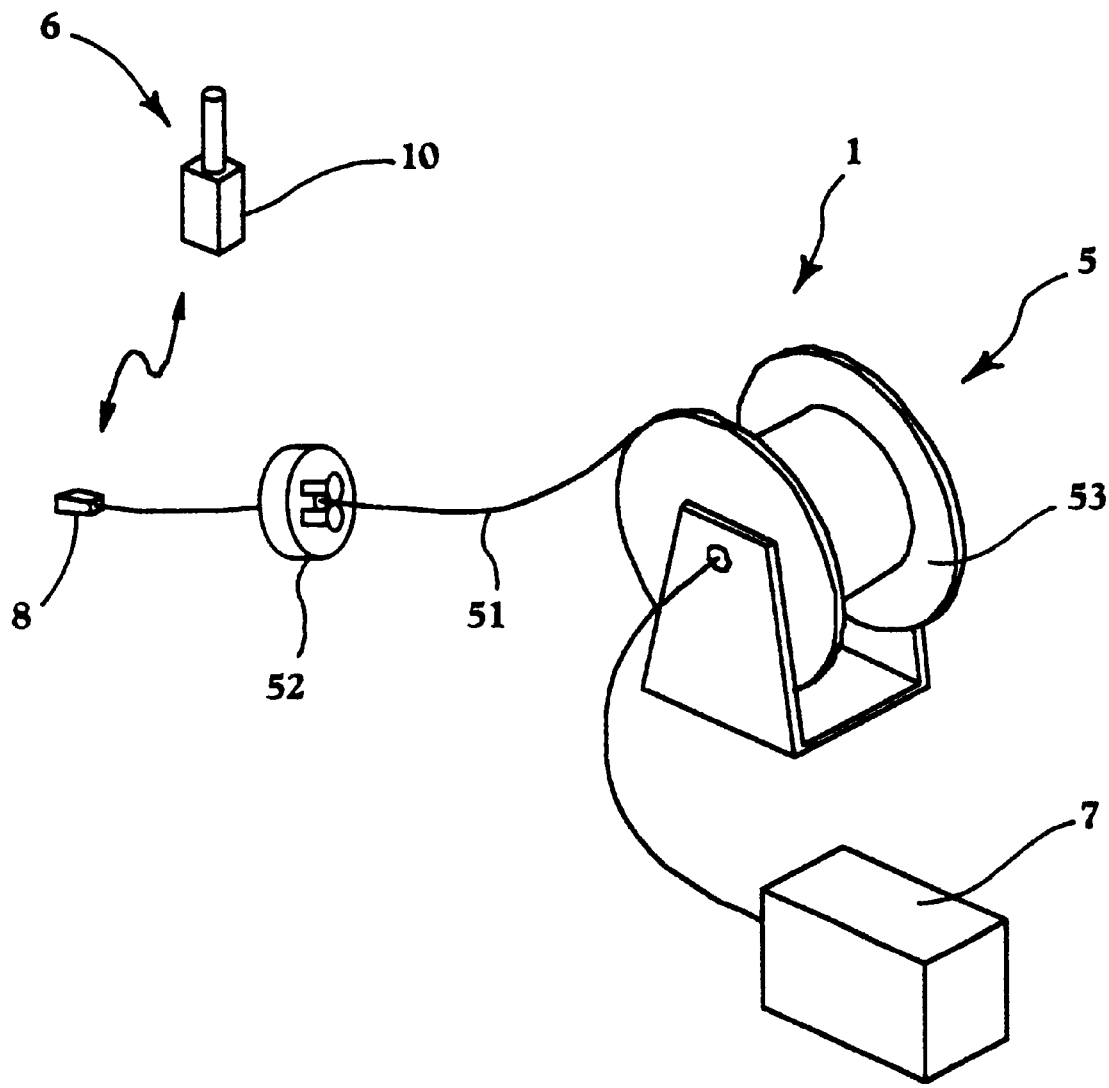
FIG. 23 is a perspective view showing some components.

One of the embodiments is shown in FIG. 22. In this embodiment, the transmitting antenna 8 of the transmitter 5 is moved by a cable 51, etc. in the pipe 1 to be inspected of a piping system, while electromagnetic waves of a frequency lower than the cut-off frequency for the pipe used as a wave guiding channel of electromagnetic waves, and the receiving antenna 10 of the receiver 6 is moved in relation with the movement of the transmitting antenna 8, to receive leaking electromagnetic waves, for inspecting the elements of the piping system. In reference to the location of the transmitting antenna 8 at which the level of electromagnetic waves received by the receiver becomes a peak, the location of the element concerned of the piping system is detected.

For such inspection, on the transmitter 5 side, the transmitter proper 7 the transmitting antenna 8 connected to the transmitter proper 7 by the cable 51 acting also as a long antenna wire, and an unwinder 52 and a winder 53 for the cable 51 are installed.

In this configuration, the cable 51 is delivered by the unwinder 52, to move the transmitting antenna 8, or the cable 51 is wound by the winder 53, to move the transmitting antenna 8, while electromagnetic waves of a frequency lower than the cut-off frequency of the pipe 1 are transmitted. Simultaneously, the receiving antenna 10 composed as described above is moved in relation with the movement of the transmitting antenna, to receive the electromagnetic waves leaking from a damaged portion, or joint, etc. of the pipe 1.

The electromagnetic waves from the transmitting antenna 8 are not propagated in the pipe 1 and attenuated greatly in a short distance. So, the quantity of electromagnetic waves leaking from a location concerned such as the damaged portion 15 or joint of the pipe is largest when the transmitting antenna 8 is nearest to the location concerned. Therefore, the level of electromagnetic waves received by the receiver 6 through the receiving antenna 10 changes very greatly when the antenna is near the location concerned, to make the peak more outstanding. So, the location concerned can be detected at higher accuracy in reference to the peak. Furthermore, since the frequency can be kept low as described above, the electromagnetic waves are attenuated less by the soil, etc. around the buried pipe, to enhance the receiving sensitivity.

In the other embodiment, the transmitter and the receiver in the above embodiment are arranged reversibly. In this method, though not illustrated, the transmitting antenna of the transmitter is moved along the pipe outside the piping system to be inspected of a piping system, while electromagnetic waves of a frequency lower than the cut-off frequency for the pipe used as a wave guiding channel of electromagnetic waves are transmitted from outside the piping system, while the electromagnetic waves entering the pipe from outside are received for inspection of elements of the piping system. In reference to the location of the receiving antenna where the level of electromagnetic waves received by the receiver becomes a peak, the location concerned of an element of the inspected piping system is detected.

In this case, since the electromagnetic waves entering from the transmitting antenna through the location concerned are not propagated in the pipe, the level of electromagnetic waves becomes highest when the receiving antenna is nearest to the location concerned. Therefore, also in this case, the level of electromagnetic waves received by the receiving antenna changes very greatly when the antenna is near the location concerned, to make the peak more outstanding, for enhancing the accuracy in the detection of the location concerned in reference to the peak.

Furthermore, these methods can also measure the route length of the piping system by allowing the length of the cable delivered to move the antenna in the pipe to be measured by the unwinder, etc.

Also in these two methods, as in the methods described before, if electromagnetic waves as carrier waves are modulated by any proper information signals, whether the electromagnetic waves received are those transmitted by the transmitter or noise can be easily distinguished.

Moreover, in the method of moving the receiving antenna outside the pipe, if the method of turning on and off the electromagnetic waves transmitted for receiving by the receiver is applied, the influence of external noise can be decreased.

In the following embodiment, the frequency of electromagnetic waves is kept at lower than the cut-off frequency of the pipe as in the above two embodiments, but the receiving antenna or the transmitting antenna arranged in the pipe is made long to eliminate the necessity of movement.

Figure 24:
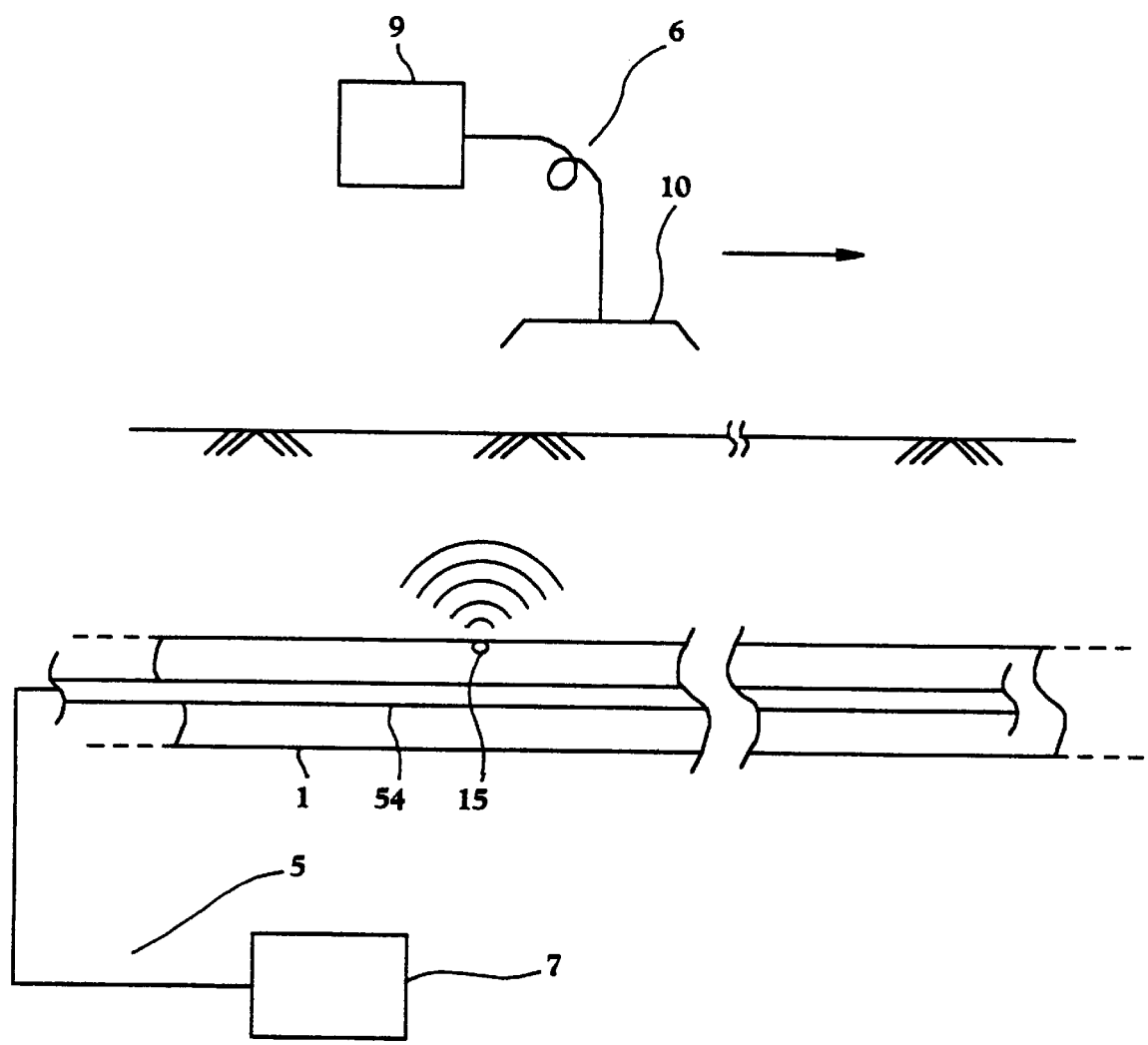
FIG. 24 is an illustration conceptually showing an inspection action by a long antenna.

FIG. 24 conceptually shows the method. As described before, a long transmitting antenna 54 with many radiating parts directional in the directions perpendicular to the axis connected in the axial direction is inserted in the pipe 1 in the testing range, and electromagnetic waves are radiated from these radiating parts. In this state, the receiving antenna, and as required the receiver proper 9 are moved along the pipe 1 in the testing range, for searching for leaking electromagnetic waves.

Since the long transmitting antenna 54 with many radiating parts directional in the directions perpendicular to the axis connected in the axial direction is inserted in the testing range of the pipe 1, to irradiate electromagnetic waves from the respective radiating parts, the receiving antenna 10 only can be moved along the pipe outside the pipe in the testing range, to search for the leaking electromagnetic waves. Since the electromagnetic waves are not required to be propagated in the pipe which can be act as a circular wave guiding channel, the frequency used is not limited to be higher than the cut-off frequency for the circular wave guiding tube.

Therefore, the advantage attributable to the low frequency of electromagnetic waves used, that attenuation by soil, etc. can be kept small can be obtained.

The long transmitting antenna 54 used in this method can be a leakage coaxial cable or twisted pair leakage cable as used for mobile communication in a tunnel, etc. Such a cable can be inserted into the pipe 1, using an insertion mechanism, etc. which can be a conventionally widely used drive cable for an in-tube tester, etc. with the gas pipe kept active.

Furthermore, the long transmitting antenna 54 can keep the length of one helical turn very smaller than the wavelength of the electromagnetic waves radiated or can keep the length of one helical turn at n times the wavelength (n is an integer of 2 or more) with its directionality kept in a direction perpendicular to the axis. A cable obtained by covering the helical wire with an insulator can be treated like the above mentioned cables.

Moreover, the transmitting antenna 54 can also be formed by connecting many small antennas to form a cable.

In the above method, the transmitting antenna is long and arranged in the pipe, but the receiving antenna can be made long and arranged in the pipe, while the transmitting antenna is moved outside the pipe along the pipe, for transmitting electromagnetic waves.

In these two methods, as done in the other methods described before, if the electromagnetic waves as carrier waves can be modulated by proper information signals, whether the electromagnetic waves received are the electromagnetic waves transmitted by the transmitter or noise can be easily distinguished. Furthermore, the level of electromagnetic waves received and the receiving sensitivity can also be properly adjusted.

When the receiving antenna is moved outside the pipe, the transmitted electromagnetic waves can be turned on and off to be received by the receiver, for decreasing the influence of external noise.

Industrial Applicability

Since the present invention is as described above, if the piping system to be inspected is, for example, a city gas supply system, the leak of gas from a gas pipe is detected in reference to the electromagnetic waves leaking from a point where gas leak occurs, not in reference to the gas leak. Therefore, the present invention is useful to accurately detect the point of gas leak, and can also be applied to detect the locations of other elements such as joints of the piping system and also the lengths of routes. The present invention can also be applied for detecting damaged portions, etc. of pipes of various piping systems.

We claim:

1. A method for detecting and locating faults and leaks in an existing underground piping system using electromagnetic waves, consisting essentially of moving a transmitting antenna of a transmitter outside the underground piping system along the direction of the pipe to be inspected, to transmit electromagnetic waves from outside the piping system; moving a receiving antenna of a receiver inside the pipe in relation to the movement of the transmitting antenna, to receive the electromagnetic waves entering the piping system from outside, for detecting faults and leaks in the piping system, detecting the location of leaks and faults in underground piping system being inspected, by sensing a peak in the level of electromagnetic waves when the transmitting antenna and receiving antenna are nearest faults or leaks.

2. A method for detecting faults and leaks in an existing underground piping system using electromagnetic waves, according to claim 1, wherein the receiving of entering electromagnetic waves by the receiver is effected when the drive of electromagnetic waves from the transmitter is in ON state, and is effected also when the drive of electromagnetic waves from the transmitter is temporarily in OFF state, and the signals received in OFF state are compared with the signals received in ON state, to distinguish the electromagnetic waves transmitted by the receiver.

3. The method for detecting and locating faults and leaks in an existing underground piping system using electromagnetic waves, according to claim 1, wherein the electromagnetic waves entering the piping system from outside to be propagated by the transmitter in the piping system inspected are modulated.

4. The method for detecting and locating faults and leaks in an existing underground piping system using electromagnetic waves, according to claim 1, wherein the transmitter is provided with an adjusting device for varying the intensity of the transmitted electromagnetic waves.

5. The method for detecting and locating faults and leaks in an existing underground piping system using electromagnetic waves, according to claim 3, wherein the electromagnetic waves are modulated by human recognizable information signals.

6. The method for detecting and locating faults and leaks in an existing underground piping system using electromagnetic waves, according to claim 4, wherein the adjusting device is varied in response to the level of electromagnetic waves received by the receiver.

7. The method for detecting and locating faults and leaks in an existing underground piping system using electromagnetic waves, according to claim 1, wherein the piping systems being inspected include underground pipes, and locations to be detected are damaged portions comprising holes in the pipe formed by corrosion.

8. The method for detecting and locating faults and leaks in an existing underground piping system using electromagnetic waves, according to claim 1, wherein the elements of the piping system to be inspected are unexposed joints, and the locations to be detected are the locations of the joints themselves.

9. The method for detecting and locating faults and leaks in an existing underground piping system using electromagnetic waves, according to claim 1, wherein the level of electromagnetic waves received by the receiver is referred to for estimating the state of each joint to be inspected.

10. The method for detecting and locating faults and leaks in an existing underground piping system using electromagnetic waves, according to claim 9, wherein electromagnetic waves entering the pipe from the joint to be inspected are received by the receiver, to detect the location of the joint, and the level of the electromagnetic waves received is referred to for estimating the condition of the joint.

11. A method for detecting and locating faults and leaks in an existing underground piping system using electromagnetic waves, consisting essentially of the steps of moving a transmitting antenna of a transmitter along the pipe to be inspected outside the piping system, while transmitting electromagnetic waves having a frequency lower than the cut-off frequency for the pipe used as a wave guiding channel of electromagnetic waves, from outside the piping system; moving a receiving antenna of a receiver inside the pipe in relation to the movement of the transmitting antenna, to receive the electromagnetic waves entering the pipe from outside, for inspecting elements of the piping system; and detecting and locating faults and leaks in the piping system to be inspected, by peaks in the level of electromagnetic waves received when the receiver antenna and transmitting antenna are nearest the location of the faults and leaks.

12. The method for detecting and locating faults and leaks in an existing underground piping system using electromagnetic waves, according to claim 11, wherein the electromagnetic waves transmitted by the transmitting antenna of the transmitter are modulated.

13. The method for detecting and locating faults and leaks in an existing underground piping system using electromagnetic waves, according to claim 12, wherein the electromagnetic waves are modulated by human recognizable information signals.

14. The method for detecting and locating faults and leaks in an existing underground piping system using electromagnetic waves, according to claim 11, wherein the reception of electromagnetic waves entering the pipe by the receiver is effected when the transmission of electromagnetic waves by the transmitter is in ON state, and is also effected when the transmission of electromagnetic waves by the transmitter is temporarily in OFF state, and the signals received in OFF state are compared with the signals received in ON state, to distinguish the electromagnetic waves caused by leaking.

15. The method for detecting and locating faults and leaks in an existing underground piping system using electromagnetic waves, according to claim 11, wherein the transmitter is provided with an adjusting device for varying the intensity of the transmitted electromagnetic waves.

16. The method for detecting and locating faults and leaks in an existing underground piping system using electromagnetic waves, according to claim 15, wherein the adjusting device is varied in response to the level of electromagnetic waves received by the receiver.

17. The method for detecting and locating faults and leaks in an existing underground piping system using electromagnetic waves, according to claim 11, wherein the elements of the piping system to be inspected are pipes, and the locations to be detected are damaged portions comprising holes formed by corrosion in the pipes.

18. The method for detecting and locating faults and leaks in an existing underground piping system using electromagnetic waves, according to claim 11, wherein the elements of the piping system to be inspected are unexposed joints, and the locations to be detected are the locations of the joints themselves.

19. The method for detecting and locating faults and leaks in an existing underground piping system using electromagnetic waves, according to claim 11, wherein the level of electromagnetic waves received by the receiver are used in estimating the condition of each joint to be inspected.

20. The method for detecting and locating faults and leaks in an existing underground piping system using electromagnetic waves, according to claims 19, wherein the electromagnetic waves entering the pipe from each joint inspected are received to detect the location of the joint, and the level of the electromagnetic waves received is used for estimating the condition of the joint.

* * * * *